US010679343B2

(12) United States Patent
Matsumura et al.

(10) Patent No.: US 10,679,343 B2
(45) Date of Patent: Jun. 9, 2020

(54) OPHTHALMIC IMAGE PROCESSING APPARATUS AND OPHTHALMIC IMAGE PROCESSING PROGRAM

(71) Applicant: NIDEK CO., LTD., Gamagori, Aichi (JP)

(72) Inventors: Keisuke Matsumura, Aichi (JP); Hironori Koike, Aichi (JP); Kota Kadokawa, Aichi (JP)

(73) Assignee: NIDEK CO., LTD., Gamagori, Aichi (JP)

(*) Notice: Subject to any disclaimer, the term of this patent is extended or adjusted under 35 U.S.C. 154(b) by 18 days.

(21) Appl. No.: 15/447,372

(22) Filed: Mar. 2, 2017

(65) Prior Publication Data

US 2017/0256054 A1 Sep. 7, 2017

(30) Foreign Application Priority Data

Mar. 3, 2016 (JP) .................. 2016-041609
Mar. 3, 2016 (JP) .................. 2016-041610
Jun. 27, 2016 (JP) .................. 2016-126678

(51) Int. Cl.
*A61B 3/15* (2006.01)
*G06T 7/00* (2017.01)
(Continued)

(52) U.S. Cl.
CPC .......... *G06T 7/0012* (2013.01); *A61B 3/0025* (2013.01); *A61B 3/152* (2013.01);
(Continued)

(58) Field of Classification Search
CPC . G06T 2207/20221; G06T 2207/10101; G06T 2207/30041; A61B 3/102;
(Continued)

(56) References Cited

U.S. PATENT DOCUMENTS 6,082,859 A * 7/2000 Okashita .............. A61B 3/0091
351/206
7,301,644 B2 * 11/2007 Knighton ............... A61B 3/102
356/479
(Continued)

FOREIGN PATENT DOCUMENTS

JP          5-324785 A     12/1993
JP       2004-357803 A    12/2004
(Continued)

OTHER PUBLICATIONS

Chaudhary et al., Investigation and visualization of scleral channels created with Femtosecond laser in enucleated human eyes using 3D Optical Coherence Tomography images, Mar. 26, 2007 (retr Oct. 16, 2018), Proceed Ophthalmic Technologies XVII, SPIE vol. 6426, 11 total pg. https://doi.org/10.1117/12.701297 (Year: 2007).*

(Continued)

*Primary Examiner* — Andrew M Moyer
*Assistant Examiner* — Dennis Rosario
(74) *Attorney, Agent, or Firm* — Sughrue Mion, PLLC

(57) ABSTRACT

An ophthalmic image processing apparatus that processes pieces of image data of a subject eye which are acquired by a plurality of ophthalmic examination apparatuses including a first ophthalmic examination apparatus obtaining first image data of the subject eye and a second ophthalmic examination apparatus obtaining second image data of the subject eye includes: a processor; and memory storing computer readable instructions, when executed by the processor, causing the ophthalmic image processing apparatus to execute: setting process of setting image types for the first image data and the second image data that form a registration image; and image processing process of generating the registration image in which the first image data and the second image data which correspond to the image types set (Continued)

in the setting process are superimposed on each other, and outputting the generated registration image.

19 Claims, 14 Drawing Sheets

(51) Int. Cl.
*A61B 3/00* (2006.01)
*G06T 11/60* (2006.01)
*A61B 3/18* (2006.01)

(52) U.S. Cl.
CPC ............... *G06T 11/60* (2013.01); *A61B 3/18* (2013.01); *G06T 2207/10101* (2013.01); *G06T 2207/30041* (2013.01)

(58) Field of Classification Search
CPC ....... A61B 3/0025; A61B 5/0066; A61B 3/14; A61B 3/0058; A61B 6/463; A61B 2090/3735; A61B 3/12; A61B 3/0041; A61B 3/0091; A61B 3/10; A61B 3/0033; A61B 5/14555; A61B 3/152; G01B 9/02091
See application file for complete search history.

(56) References Cited

U.S. PATENT DOCUMENTS

| | | | | |
|---|---|---|---|---|
| 7,575,321 | B2 * | 8/2009 | Newman | A61B 3/0058 351/205 |
| 8,223,143 | B2 * | 7/2012 | Dastmalchi | A61B 3/102 345/418 |
| 8,256,897 | B2 * | 9/2012 | Huang | A61B 3/102 351/205 |
| 8,401,246 | B2 * | 3/2013 | Huang | A61B 3/0058 351/206 |
| 9,456,748 | B2 * | 10/2016 | Imamura | A61B 3/152 |
| 9,545,196 | B2 * | 1/2017 | Abramoff | A61B 3/102 |
| 10,219,693 | B2 * | 3/2019 | Mikaelian | A61B 3/024 |
| 2007/0229659 | A1 | 10/2007 | Yamaguchi | |
| 2008/0100612 | A1 | 5/2008 | Dastmalchi et al. | |
| 2009/0033870 | A1 | 2/2009 | Hangai et al. | |
| 2010/0145231 | A1 | 6/2010 | Takahashi et al. | |
| 2011/0046480 | A1 | 2/2011 | Yonezawa | |
| 2011/0279665 | A1 | 11/2011 | Yamaguchi | |
| 2014/0063453 | A1 | 3/2014 | Natsuhori et al. | |
| 2014/0112562 | A1 | 4/2014 | Yamakawa et al. | |
| 2014/0221827 | A1 * | 8/2014 | Motaghiannezam | G01N 21/4795 600/425 |
| 2014/0379362 | A1 | 12/2014 | Morishima et al. | |
| 2015/0168127 | A1 | 6/2015 | Takeno et al. | |
| 2015/0371383 | A1 | 12/2015 | Chabrier et al. | |
| 2015/0374228 | A1 | 12/2015 | Satake et al. | |
| 2016/0367130 | A1 | 12/2016 | Natsuhori et al. | |
| 2017/0256054 | A1 * | 9/2017 | Matsumura | G06T 7/0012 |
| 2018/0132725 | A1 * | 5/2018 | Vogl | G06T 7/0012 |
| 2018/0172426 | A1 | 6/2018 | Takeno et al. | |
| 2019/0076012 | A1 * | 3/2019 | Kobayashi | A61B 3/10 |

FOREIGN PATENT DOCUMENTS

| | | |
|---|---|---|
| JP | 2005-301816 A | 10/2005 |
| JP | 2007-289657 A | 11/2007 |
| JP | 2010-246779 A | 11/2010 |
| JP | 2010-253243 A | 11/2010 |
| JP | 2012-254164 A | 12/2012 |
| JP | 2013-116366 A | 6/2013 |
| JP | 2013-154120 A | 8/2013 |
| JP | 2013-215563 A | 10/2013 |
| JP | 2014-18251 A | 2/2014 |
| JP | 2014-61280 A | 4/2014 |
| JP | 2015-131107 A | 7/2015 |
| JP | 2016-10658 A | 1/2016 |
| JP | 2016-101297 A | 6/2016 |
| WO | 2011/091253 A2 | 7/2011 |
| WO | 2015/165989 A2 | 11/2015 |

OTHER PUBLICATIONS

Communication issued by the European Patent Office dated Oct. 9, 2017 in counterpart European Patent Application No. 17158927.8.
Communication dated Nov. 19, 2019, issued by the Japanese Patent Office in counterpart Japanese Application No. 2016-041610.
Office Action dated Jan. 14, 2020 by the Japanese patent Office in counterpart Japanese Patent Application No. 2016-126676.
Office Action dated Dec. 17, 2019 by the Japanese Patent Office in counterpart Japanese Patent Application No. 2016-041609.

\* cited by examiner

OPHTHALMIC IMAGE PROCESSING APPARATUS AND OPHTHALMIC IMAGE PROCESSING PROGRAM

CROSS REFERENCE TO RELATED APPLICATIONS

This application is based upon and claims the benefit of priorities of Japanese Patent Application No. 2016-041609 filed on Mar. 3, 2016, Japanese Patent Application No. 2016-041610 filed on Mar. 3, 2016 and Japanese Patent Application No. 2016-126678 filed on Jun. 27, 2016, the contents of which are incorporated herein by reference in its entirety.

BACKGROUND

The present disclosure relates to an ophthalmic image processing apparatus that processes image data acquired by an ophthalmic examination apparatus, and an ophthalmic image processing program.

There has been known a technique for superimposing pieces of image data acquired by a plurality of ophthalmic examination apparatuses on each other (see, for example, JP-A-2013-116366).

However, in the related art described above, there may be the following possibility. For example, there is no degree of freedom in a type of superimposition image, and thus there is a possibility that it is difficult to perform diagnosis from multilateral viewpoints. In addition, visibility in the superimposition image is not considered, and thus there is a possibility that it is difficult for an examiner to visually perceive the superimposition image.

SUMMARY

An object of this disclosure is to provide an ophthalmic image processing apparatus and an ophthalmic image processing program which are capable of solving at least one of the problems of the related art.

In order to solve the above-described problems, this disclosure has the following configuration.

An ophthalmic image processing apparatus that processes pieces of image data of a subject eye which are acquired by a plurality of ophthalmic examination apparatuses including a first ophthalmic examination apparatus obtaining first image data of the subject eye and a second ophthalmic examination apparatus obtaining second image data of the subject eye, the ophthalmic image processing apparatus comprising:
 a processor; and
 memory storing computer readable instructions, when executed by the processor, causing the ophthalmic image processing apparatus to execute:
 setting process of setting image types for the first image data and the second image data that form a registration image; and
 image processing process of generating the registration image in which the first image data and the second image data which correspond to the image types set in the setting process are superimposed on each other, and outputting the generated registration image.

DESCRIPTION OF ILLUSTRATIVE EMBODIMENTS

Figure 1:
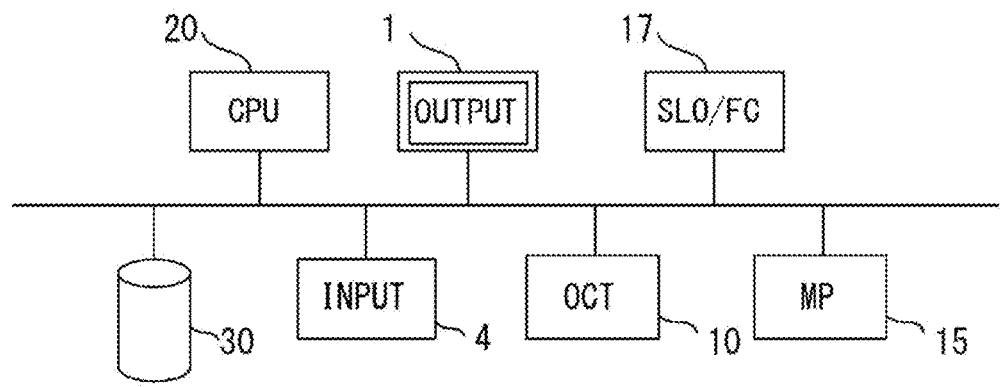
FIG. 1 is a block diagram illustrating an example of an ophthalmic image processing apparatus according to this example.
Figure 2:
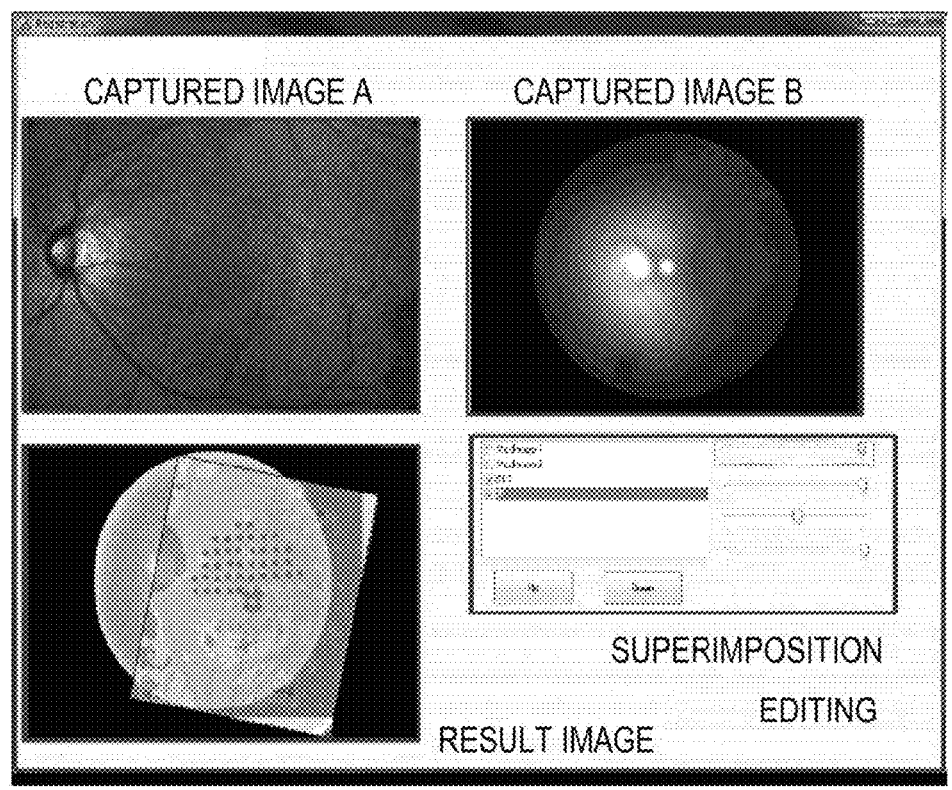
FIG. 2 is a diagram illustrating an example of a registration screen according to this example.

Embodiments of this disclosure will be described with reference to the accompanying drawings. FIGS. 1 to 16 are diagrams related to examples of this embodiment. Meanwhile, items classified by "< >" described below may be used independently of or in relation to each other.

An ophthalmic image processing apparatus can process an image acquired by an ophthalmic examination apparatus. The image processing may be performed by an image processing unit (for example, a processor 20). The processor 20 may be, for example, a CPU provided in the ophthalmic examination apparatus, in addition to a CPU of a personal computer.

An instruction reception unit (for example, the processor 20) has a function of receiving an instruction from an examiner. The instruction reception unit can receive an operation signal from a user interface (for example, an operation unit 4) such as a touch panel, a mouse, or a keyboard.

The image processing unit (for example, the processor 20) outputs an image. An output destination may be an output unit (output device) such as a display unit (for example, a display unit 1) or a printer, or may be a storage unit (storage device) such as a hard disk or a USB memory.

The storage unit (for example, a storage unit 30) may be, for example, a storage unit provided in the main body of the ophthalmic examination apparatus, a storage unit provided in an external server, a storage unit provided in a personal computer, or the like. A personal computer may be used as the ophthalmic image processing apparatus, or may be a dedicated apparatus. Meanwhile, the ophthalmic examination apparatus may also serve as an ophthalmic image processing apparatus.

The ophthalmic image processing apparatus and the ophthalmic examination apparatus are connected to each other in a signal exchangeable state. For example, an image acquired by a first ophthalmic examination apparatus (for example, an ophthalmic OCT device 10) and an image acquired by a second ophthalmic examination apparatus (for example, a visual field examination apparatus 15) are stored in the storage unit.

<Program>

This apparatus may include a control unit (for example, the processor 20) which performs various control processes, and a storage unit that stores an ophthalmic image processing program. The processor 20 can perform processing in accordance with a program. The control unit may also serve as an image processing unit.

<Registration Process (See FIG. 2)>

The ophthalmic image processing apparatus may have a function of superimposing a plurality of pieces of image data on each other, or may acquire a registration image which is a superimposition image in which a plurality of pieces of image data are superimposed on each other. In the following description, a function of superimposing a plurality of pieces of image data on each other may be realized as a function of superimposing a plurality of pieces of image data on each other, and a registration image which is a superimposition image in which a plurality of pieces of image data are superimposed on each other may be realized as a registration image which is an image in which a plurality of pieces of image data are superimposed on each other.

In this case, this apparatus may include an image processing unit (registration function) which displays images acquired by a plurality of ophthalmic examination apparatuses in an overlapping manner (superimposition display). The image processing unit may generate a registration image which is an image in which first image data and second image data are superimposed on each other, and may output the generated registration image.

The first image data may be image data acquired by the first ophthalmic examination apparatus. The second image data may be image data acquired by the second ophthalmic examination apparatus. The second ophthalmic examination apparatus may be an ophthalmic examination apparatus different from the first ophthalmic examination apparatus.

The ophthalmic image processing apparatus may include a setting unit that sets an image type in the first image data and the second image data that constitute the registration image. The image processing unit may generate and output a registration image in which the first image data and the second image data corresponding to the set image type are superimposed on each other. The image processing unit may generate the registration image based on setting conditions that are set by the setting unit.

The setting unit may include an instruction reception unit that receives an instruction from an examiner, and may perform a setting process based on an instruction signal received from the instruction reception unit. In addition, the setting unit may set an image type in accordance with setting conditions that are set in advance. In this case, for example, the setting conditions may be set in accordance with specifications of reports, and an image type may be set in accordance with specifications of a selected report. Meanwhile, image types capable of being set as pieces of image data constituting a registration image may include various image types. According to the setting of the image types, for example, it is possible to obtain an examiner's desired registration image and to perform multilateral confirmation.

<Change of Setting of Registration Image (See FIG. 3)>

An instruction from the operation unit for changing the setting of the registration image may be received in a state where a registration image is displayed on a display unit, and it may be possible to change the setting of the registration image. An image processing unit may generate the registration image based on the change of the setting.

<Setting in Order of Layer>

In this apparatus, it may be possible to change the setting of the order in which first image data and second image data are superimposed on each other. For example, as the order of which the setting is changeable, it may be possible to change the setting of any one of a first registration image in which the second image data is superimposed on the first image data and a second registration image in which the first image data is superimposed on the second image data. Accordingly, an examiner can select the order of superimposition in consideration of visibility, the purpose of diagnosis, and the like.

The instruction reception unit may receive an instruction signal from the operation unit for setting the order of layer in which the first image data and the second image data are superimposed on each other when a registration image is generated. The image processing unit may generate the registration image based on the selected order of layer. Accordingly, an examiner can select a desired order of superimposition in consideration of visibility, the purpose of diagnosis, and the like. Meanwhile, in a case where any one of the first image data and the second image data includes a plurality of pieces of image data, it may be possible to set the order of superimposition of three or more pieces of image data.

<Setting of Transmittance>

In this apparatus, when a registration image is generated, it may be possible to change the setting of a transmittance of at least one of first image data and second image data. The transmittance may be changeable in a range of 0% to 100%. Accordingly, in the registration image, it is possible to easily confirm an image formed on the back of another image data.

The instruction reception unit may receive an instruction signal from the operation unit for setting the transmittance of at least one of the first image data and the second image data. The image processing unit may generate a registration image based on selected transmittance. Accordingly, the registration image set to have an examiner's desired transmittance is obtained. Meanwhile, the instruction reception unit may receive a selection instruction for selecting transmittances of respective pieces of image data.

<Setting of Brightness or Contrast>

In this apparatus, when a registration image is generated, it may be possible to change the setting of a brightness or a contrast of at least one of first image data and second image data. Accordingly, it is possible to adjust the visibility of the registration image.

The instruction reception unit may receive an instruction signal from the operation unit for setting the brightness or contrast of at least one of the first image data and the second image data. The image processing unit may generate the registration image based on selected brightness or contrast.

Accordingly, it is possible to set the registration image which is easily viewed by an examiner.

<Selection of Image Data>

In this apparatus, an instruction form the operation unit for selecting image data constituting a registration image may be received in a state where the registration image is displayed on the display unit, and it may be possible to select the image data constituting the registration image. The image processing unit may generate the registration image based on setting conditions that are set by the selection.

<Setting of Superimposition Region (See FIG. 14)>

In this apparatus, when a registration image is generated, it may be possible to set a superimposition region in which first image data and second image data are superimposed on each other. Accordingly, visibility with respect to a region to which an examiner gives attention is improved, and thus it is possible to acquire an examiner's desired registration image.

The instruction reception unit may receive an instruction signal from the operation unit for setting the superimposition region in which the first image data and the second image data are superimposed on each other. The image processing unit may generate a registration image based on the set superimposition region. Accordingly, the registration image which is set in the examiner's desired superimposition region is obtained.

In more detail, any region can be set on the registration image, and an image type to be output within the set region can be arbitrarily selected from image types constituting the registration image. Meanwhile, the number of image types to be output with respect to the set region is not limited to one, and may be two or more. In this case, the examiner may set the region, or a superimposition region may be automatically set based on setting conditions that are set in advance. In this case, it may be possible to change the setting of the superimposition region.

Figure 14:
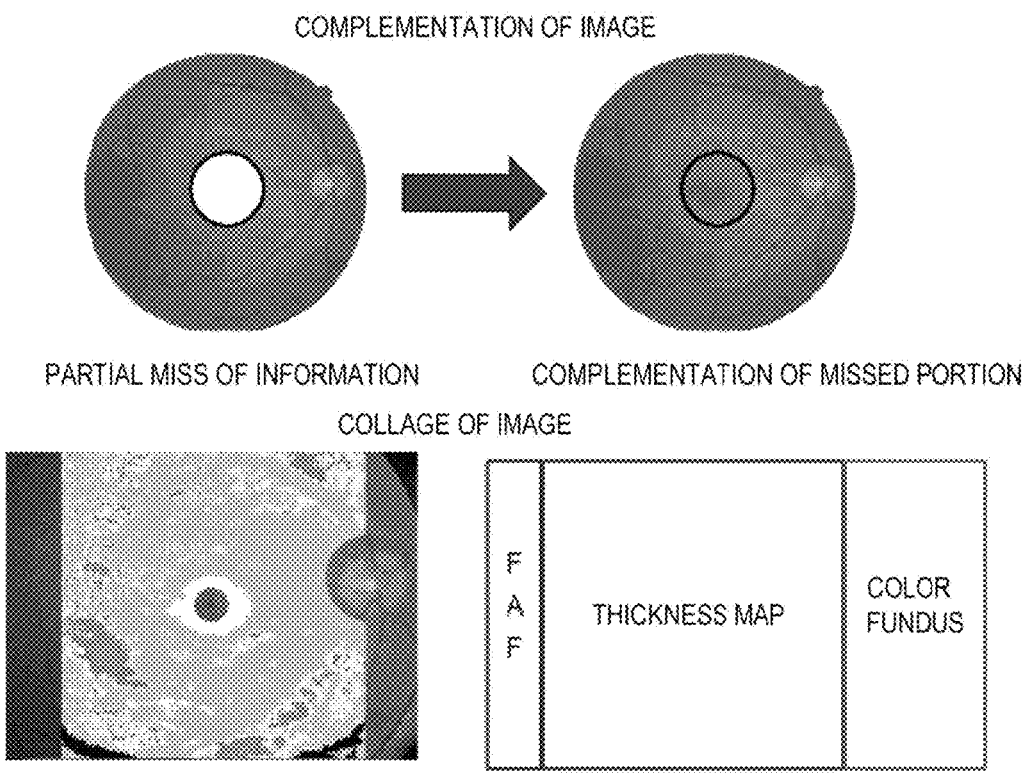
FIG. 14 is a diagram illustrating an example of a case where a superimposition region according to this example is set.
Figure 15:
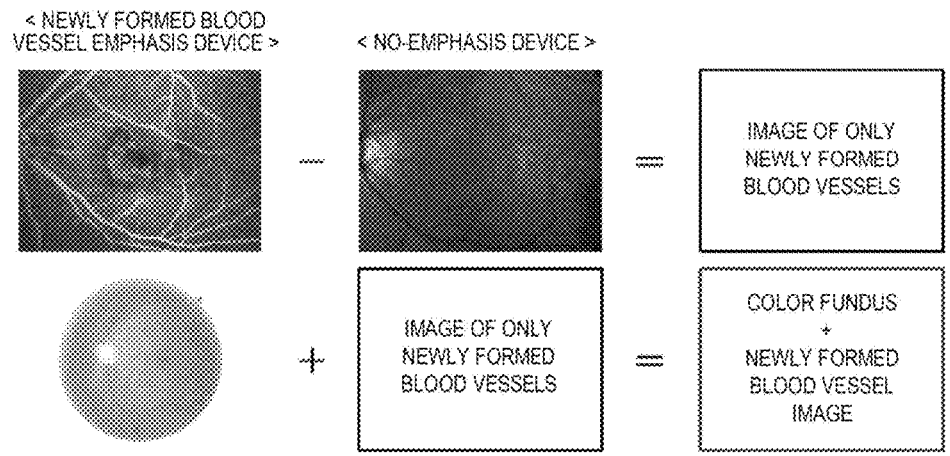
FIG. 15 is a diagram illustrating an example of a case where a characteristic image according to this example is generated.

As illustrated in FIG. 14, the above-described method may be used for the complement of a missed portion in image data, or collage using a plurality of images may be performed. In the collage of FIG. 14, a registration image in which at least one of a first fundus front image (for example, an autofluorescent image) and a second fundus front image (for example, a color fundus image) and a map image (for example, an OCT map image) are superimposed on each other is displayed, the first fundus front image is displayed in a first display region different from the registration image as a single body, and the second fundus front image is displayed in a second display region different from the registration image as a single body.

<Generation of Characteristic Image (See FIG. 15)>

The image processing unit may perform difference processing (for example, a process of obtaining a difference or a ratio between luminance values) between first image data and second image data in a state where the first image data and the second image data are superimposed on each other. The image processing unit may generate a difference image based on the difference processing, and may output the difference image. Accordingly, a characteristic image having other portions subtracted therefrom is obtained.

For example, the image processing unit can perform image difference processing between a first fundus front image including newly formed blood vessels (for example, an OCT motion contrast En face image, a fluorescent contrast image using a contrast medium, or the like) and a second fundus front image (for example, an OCT En face image, an autofluorescent image, or the like) in which newly formed blood vessels are less imaged than in the first fundus front image to thereby obtain a characteristic image having other fundus blood vessels subtracted therefrom with respect to newly formed blood vessels.

Further, the image processing unit may generate a registration image in which the obtained difference image and another image are superimposed on each other. Thereby, it is possible to obtain an examiner's desired new registration image. For example, the image processing unit may generate a registration image in which a characteristic image having other fundus blood vessels subtracted therefrom with respect to the above-described newly formed blood vessels and a color fundus front image are superimposed on each other.

<Report (See FIG. 4)>

In this apparatus, it may be possible to generate a report including a registration image (for example, a custom report). The report including the registration image may be a report using only one or a plurality of registration images, or may be a report including another image acquired by the ophthalmic examination apparatus in addition to one or a plurality of registration images. An integrated report is generated by integrally displaying the registration image and the another image acquired by the ophthalmic examination apparatus, and an examiner can effectively perform diagnosis using the registration image. In this case, it may be possible to set the type of another image.

<Superimposition of Map Image (See FIG. 5)>

The image processing unit may acquire first map image data, which is a map image of a subject eye which is acquired by the first ophthalmic examination apparatus, and first front image data, which is first front image data being a front image of the subject eye which is acquired by the first ophthalmic examination apparatus and is associated with the first map image data, from the storage unit as first image data.

The image processing unit may acquire second map image data, which is a map image of the subject eye which is acquired by the second ophthalmic examination apparatus, and a second front image data, which is a front image of the subject eye which is acquired by the second ophthalmic examination apparatus, from the storage unit as second image data.

Figure 5:
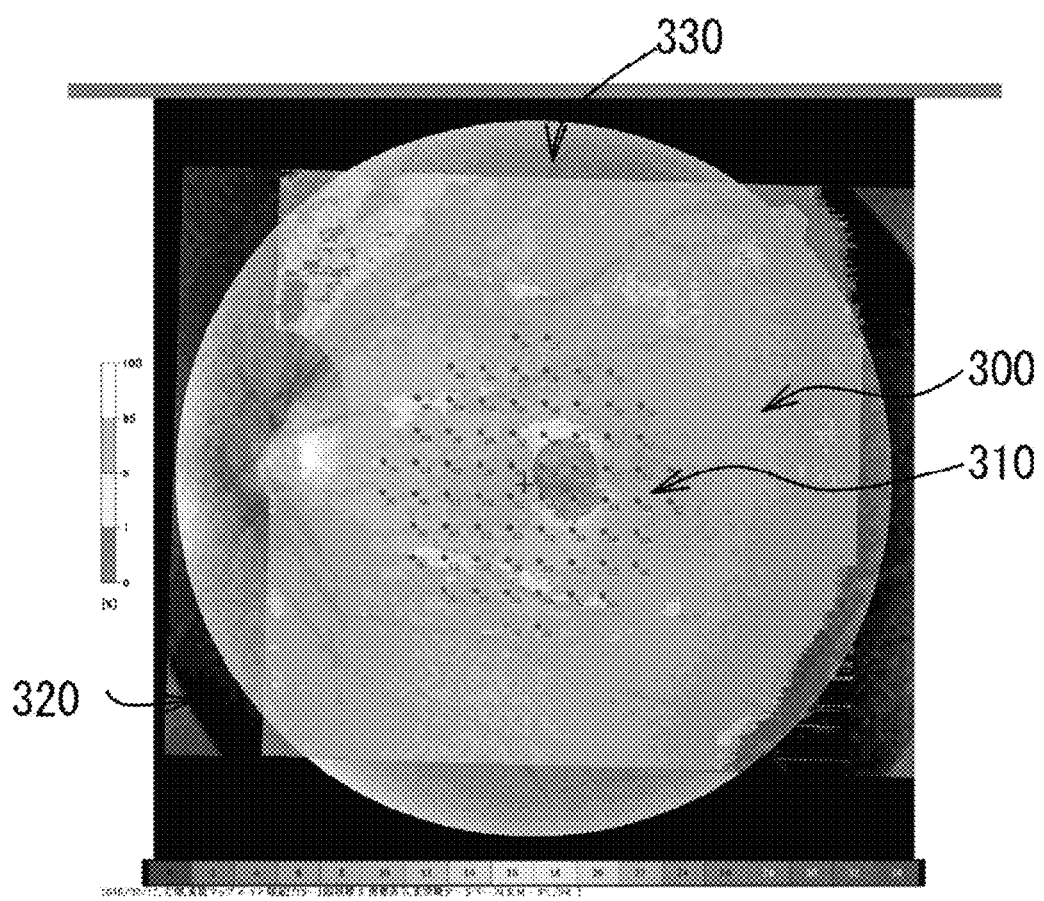
FIG. 5 is a diagram illustrating an example of a registration image according to this example.

The image processing unit may generate a registration image in which the first map image data, the first front image data, the second map image data, and the second front image data are superimposed on each other (see FIG. 5).

In this case, it may be possible to change the setting of an image type in at least one of the first map image data and the second map image data. In addition, the image processing unit may perform alignment between the first front image data and the second front image data to thereby perform alignment between the first map image data and the second map image data.

<OCT Map Image (or En-Face Image) and Visual Field Map Image (See FIGS. 5, 10, and 11)>

Registration according to this embodiment is advantageous when first image data obtained by the first ophthalmic examination apparatus including at least an OCT and second image data obtained by the second ophthalmic examination apparatus having at least a visual field measurement function are superimposed on each other.

The image processing unit may generate a registration image in which an OCT two-dimensional image (for example, an analysis map image in which a fundus is analyzed, or an OCT En face image) which is acquired by the first ophthalmic examination apparatus and a map image of a subject eye which is acquired by the second ophthalmic examination apparatus are superimposed on each other.

For example, the first ophthalmic examination apparatus may be an ophthalmic OCT device including an OCT optical system for capturing a fundus tomographic image and a first imaging optical system for capturing a fundus front image. The first imaging optical system may be an SLO or may be a fundus camera. In addition, the OCT optical system may also be configured to serve as the first imaging optical system.

The first image data may be an OCT two-dimensional image (for example, an analysis map image in which a fundus is analyzed, or an OCT En face image) and a front image which is a first fundus front image acquired by the first imaging optical system and is associated with the OCT two-dimensional image.

For example, the second ophthalmic examination apparatus may be an ophthalmic examination apparatus including a visual field measurement optical system for measuring a visual field and a second imaging optical system for capturing a fundus front image. The second image data may be a visual field map image acquired by the visual field measurement optical system and a fundus front image which is a second fundus front image acquired by the second imaging optical system and is associated with the map image.

In this case, alignment between the OCT two-dimensional image and the visual field map image may be performed by matching the first fundus front image acquired by the first imaging optical system and the second fundus front image acquired by the second imaging optical system to each other. In this case, a deviation in a magnification between the OCT two-dimensional image and the visual field map image may be corrected by adjusting a magnification between the first fundus front image and the second fundus front image.

In addition, unconformity between images due to a difference between the imaging optical systems may be corrected by transforming at least one of the fundus front images. In this case, the image processing unit may transform the first fundus front image with respect to the second fundus front image, and may transform the OCT two-dimensional image with respect to the visual field map image. In this case, since the OCT two-dimensional image is continuously formed, visibility is secured in spite of the transformation of the image. On the other hand, a visual field map image (for example, visibility maps) is generally discretely displayed at fixed intervals, and thus there is a possibility that it is difficult to view the visual field map image due to transformation. Consequently, the OCT two-dimensional image is transformed with respect to the visual field map image, and thus the visibility of the visual field map image is maintained. As a result, the visibility of both the map images is secured.

Here, the OCT two-dimensional image (an analysis map image, an OCT En face image, or the like) which is superimposed on the visual field map image is switchable between a plurality of types, and thus it is possible to multilaterally confirm a relationship between OCT information and visual field information of a subject eye.

<Fundus Front Image and Visual Field Map Image (See FIG. 6)>

Registration according to this embodiment is advantageous when first image data obtained by the first ophthalmic examination apparatus including the first imaging optical system for capturing a fundus front image and second image data obtained by the second ophthalmic examination apparatus having at least a visual field measurement function are superimposed on each other.

The first image data may be a first fundus front image acquired by the first imaging optical system. The number of first ophthalmic examination apparatuses to be prepared may be two or more, and it may be possible to select a fundus front image acquired by a different first ophthalmic examination apparatus.

For example, the second ophthalmic examination apparatus may be an ophthalmic examination apparatus including a visual field measurement optical system for measuring a visual field and a second imaging optical system for capturing a fundus front image. The second image data may be a visual field map image obtained by the visual field measurement optical system and a fundus front image which is a second fundus front image acquired by the second imaging optical system and is associated with the map image.

In this case, alignment between the first fundus front image acquired by the first imaging optical system and the second fundus front image acquired by the second imaging optical system may be performed by matching the fundus front images to each other. In this case, a magnification between the first fundus front image and the second fundus front image may be adjusted.

Here, the first fundus front image (for example, a fundus front image acquired by a fundus camera, a fundus front image acquired by an SLO, or a fundus front image acquired by an OCT) which is superimposed on the visual field map image may be switchable between a plurality of types, and thus it is possible to multilaterally confirm a relationship between a fundus front image and visual field information of a subject eye.

<Registration Image with Third Image Data (See FIG. 6)>

The image processing unit may generate a registration image in which third image data, which is image data of the subject eye which is acquired by a third ophthalmic examination apparatus (for example, a fundus imaging apparatus 17) which is different from the first ophthalmic examination apparatus and the second ophthalmic examination apparatus, and the first image data which is image data of the subject eye which is acquired by the first ophthalmic examination apparatus, are superimposed on each other.

In this case, it may be possible to change the setting of an image type of an image to be superimposed on the first image data between the second image data and the third image data. Meanwhile, the first ophthalmic examination apparatus may be an ophthalmic OCT device, the second ophthalmic examination apparatus may be a visual field examination apparatus, and the third ophthalmic examination apparatus may be a fundus imaging apparatus for capturing a fundus front image. The third ophthalmic examination apparatus may be any one of a fundus camera and an SLO.

<Data Output Based on Examination Date (See FIGS. 7 and 13)>

The image processing unit may process image data of a subject eye which is acquired by the ophthalmic examination apparatus to thereby generate a report including the processed image data. Meanwhile, the image processing unit may process pieces of image data of a subject eye which are acquired by a plurality of ophthalmic examination apparatuses to thereby generate a custom report including the processed pieces of image data acquired by the plurality of ophthalmic examination apparatuses.

The ophthalmic image processing apparatus may have a function of outputting image data based on a set examination date. It is possible to easily confirm a plurality of pieces of image data related to an examination date which are desired to be viewed by an examiner, by using the function.

For example, this apparatus may include a setting unit that sets an examination date of image data to be output as a report. The setting unit may be capable of manually setting the examination date of the image data to be output as a report, and may include an instruction reception unit that receives an instruction signal from an operation unit for setting an examination date to thereby perform setting based on the instruction signal. In addition, the setting unit may set the examination date in accordance with setting conditions that are set in advance. A method of setting an examination date also includes a method of setting a predetermined period of time (for example, units of weeks, units of months, units of years, or the like).

The image processing unit may acquire image data on the set examination date or within a predetermined period of time based on the examination date, from the storage unit. In this case, in a case where a predetermined period of time is set as a method of setting an examination date, the image processing unit may acquire image data included in the set predetermined period of time from the storage unit. The image processing unit may generate a report based on the acquired image data.

It may be possible to change the setting of an examination date of image data to be output as a report. The image processing unit may acquire image data on the examination date of which the setting is changed or within a predetermined period of time based on the examination date from the storage unit.

The image processing unit may generate an examination date list of which the setting can be changed by the setting unit, based on examination date data added to image data of a subject eye which is stored in the storage unit. The image processing unit may selectably display the generated examination date data on the display unit. Thereby, it is possible to smoothly perform the setting of an examination date.

Meanwhile, it may be possible to set an image type of image data to be output as a report. The image processing unit may acquire image data, being image data on the set examination date or within a predetermined period of time based on the examination date, which corresponds to the set image type, from the storage unit based on the set examination date and image type. The image processing unit may generate a report based on the acquired image data.

<Enlargement Display>

The image processing unit may enlarge a portion of image data of a subject eye which is acquired by the ophthalmic examination apparatus and may display the enlarged portion on a report. For example, the image processing unit may enlarge a specific region of the image data instead of enlarging the entire image data. Therefore, it is possible to enlarge only a portion of an image which is desired to be observed, without changing the size of a display frame of image data occupying a report output screen. Thereby, it is possible to prevent invisibleness due to being superimposed on another image on the report.

Meanwhile, the number of portions of image data to be enlarged may be one or two or more. For example, two portions of a macula and an optic disc of image data may be displayed so as to be enlarged.

The instruction reception unit may receive an instruction signal for setting a magnification (an enlargement rate or a reduction rate) and an enlarged region at the time of enlarging image data. In this case, the image processing unit may enlarge a portion of the image data based on the instruction signal received by the instruction reception unit, and may display the enlarged portion on a report. Meanwhile, the enlarged region is, for example, a region in which a portion of the image data is enlarged.

The instruction reception unit may receive a selection instruction for an examiner to select at least one piece of image data displayed on the report. Further, the image processing unit may enlarge a portion of the at least one piece of image data which is selected based on the selection instruction. Thereby, the examiner can easily enlarge a portion of desired image data on the report and can simply generate a desired report.

In this case, a portion of the image data may be enlarged by the examiner's operation. Alternatively, for example, image data may be selected by at least one piece of image data being designated by a cursor, and a process of enlarging the selected image data may be performed based on an instruction signal (for example, a wheel operation, a click operation, or the like) which is received from the instruction reception unit. In addition, for example, a process of selecting image data and enlarging the image data may be performed by operating a touch panel (for example, a pinch-out operation or a tapping operation) with respect to the at least one piece of image data. Naturally, this disclosure is not limited thereto, and the image processing unit may automatically enlarge the selected image data according to a magnification which is set in advance.

The image processing unit may arbitrarily change the magnification of the image data, which is displayed on the report, on the report. For example, the image processing unit may change the magnification of an image to 1.5 times, 2 times, 3 times, . . . , and n times. For example, the image processing unit may enlarge or reduce the image data on the report based on an instruction signal for setting a magnification which is received by the instruction reception unit.

In a case where the image processing unit enlarges a portion of the image data displayed on the report, the image processing unit may change an enlarged region of the image data, which is displayed on the report, on the report based on an instruction signal for setting the enlarged region which is received by the instruction reception unit. For example, the image processing unit may change the enlarged region of the image data, based on the instruction signal for setting the enlarged region which is received by the instruction reception unit.

For example, in a case of an image in which both a macula and an optic disc of a subject eye are seen, an enlarged region may be changed so that one of the macula and the optic disc is seen. Naturally, this embodiment is not limited to the macula or the optic disc, and the enlarged region may be changed so that a specific region such as a lesion portion or another region is seen. The image processing unit changes the enlarged region based on, for example, an examiner's instruction received from the instruction reception unit.

Meanwhile, the image processing unit may be capable of individually changing magnifications and enlarged regions of a plurality of pieces of image data on a report. For example, the image processing unit may change the magnification and the enlarged region of image data selected based on an instruction signal received by the instruction reception unit.

Meanwhile, the image processing unit may synchronize magnifications and/or enlarged regions of at least two pieces of image data with each other. For example, the image processing unit may select at least two images having magnifications and/or enlarged regions to be synchronized with each other based on an instruction signal received by the instruction reception unit, and may synchronize the magnification and/or the enlarged regions of the selected pieces of image data with each other.

The image processing unit may perform conformation to the magnification and/or the enlarged region of image data having a narrow imaging range among at least two pieces of image data displayed on a report. In this case, for example, the magnification and/or the enlarged region of image data having a wide imaging range may be automatically adjusted to the magnification and/or the enlarged region of the image data having a narrow imaging range, or may be adjusted through an examiner's manual operation.

For example, in many cases, motion contrast images of the same region which are acquired based on a plurality of OCT signals may have a narrower imaging range than that of a fundus image captured by a fundus camera or the like. In a case where different types of image data are arranged on the same report, the image processing unit may automatically adjust an enlarged region. For example, the image processing unit may adjust an enlarged region of an image having a wide imaging range (for example, a fundus camera image) in accordance with an image having a narrow imaging range (for example, a motion contrast image). Thereby, for example, an examiner can observe the fundus camera image and the like with the same magnification as those of the motion contrast image and the like.

Meanwhile, the image processing unit may adjust the magnifications and/or the enlarged regions of at least two pieces of image data to a magnification and/or an enlarged region which is set in advance. For example, the magnification and/or the enlarged region which is set in advance may be arbitrarily changed by an examiner, or may have a fixed value. Naturally, as described above, the magnifications and/or the enlarged regions may be set to be the magnification and/or the enlarged region of image data having a narrow imaging range. In this case, at least image data having a wide imaging range is set to be enlarged, and thus visibility in a region given attention is improved.

Meanwhile, image data may be acquired in a state where a portion of an image is enlarged, in addition to changing the magnification of the image on the report. In detail, for example, image data of which the magnification and the enlarged region are set in advance in the ophthalmic examination apparatus may be acquired, instead of acquiring image data having its original size acquired by the ophthalmic examination apparatus. An image having a magnification and an enlarged region that are set in advance may be displayed on the report.

Meanwhile, regarding the display on the report, for example, an image may be displayed on the display unit in a manner of being stored in the storage unit. In addition, for example, the report may be displayed on the display unit in a manner of being output to the outside or being printed. In this case, for example, as a layout of the report, a background may be displayed in white, and image data may be displayed with respect to the white background.

EXAMPLES

The storage unit 30 of the ophthalmic image processing apparatus according to this example stores pieces of image data acquired by a plurality of ophthalmic examination apparatuses (for example, the ophthalmic OCT device 10, the visual field examination apparatus 15, and the fundus imaging apparatus 17) which are connected to the apparatus. Meanwhile, the pieces of image data are classified according to patients and are stored so as to be identifiable for each patient. The stored pieces of image data can be viewed using software for image viewing, and it is also possible to generate a report including analysis results for the stored pieces of image data, and the like. The image data stored in the storage unit 30 may be captured image data acquired by the ophthalmic examination apparatus or may be map image data acquired by the ophthalmic examination apparatus. For example, the map image data is obtained by analyzing a captured image or measurement results.

The captured image and the map image obtained based on the captured image may be stored in the storage unit 30 in association with each other. In this case, the processor 20 may separate the captured image and the map image from each other and may store the separate images in the storage unit 30 as two images. Thereby, the captured image and the map image can be used as images independent of each other, which brings an advantage in generating a registration image. For example, in a case where the captured image and the map image are stored in a state of being superimposed on each other, the images are integrated with each other, and thus it is difficult to perform processing such as the independent adjustment of a transmittance or the temporary canceling of superimposition of one image. On the other hand, the images are separately stored, and thus there is an advantage in the independent adjustment of a transmittance, the temporary canceling of an image type of a portion constituting a registration image, and the like.

<Templet Generation Screen>

A type of image which is the basis of a registration image (an image constituting a registration image) may be set in advance as a template. For example, template data is stored in the storage unit 30. The template may be generated by an examiner on software, or may be provided in advance as default setting. Further, new template data may be registered through communication means.

Figure 8:
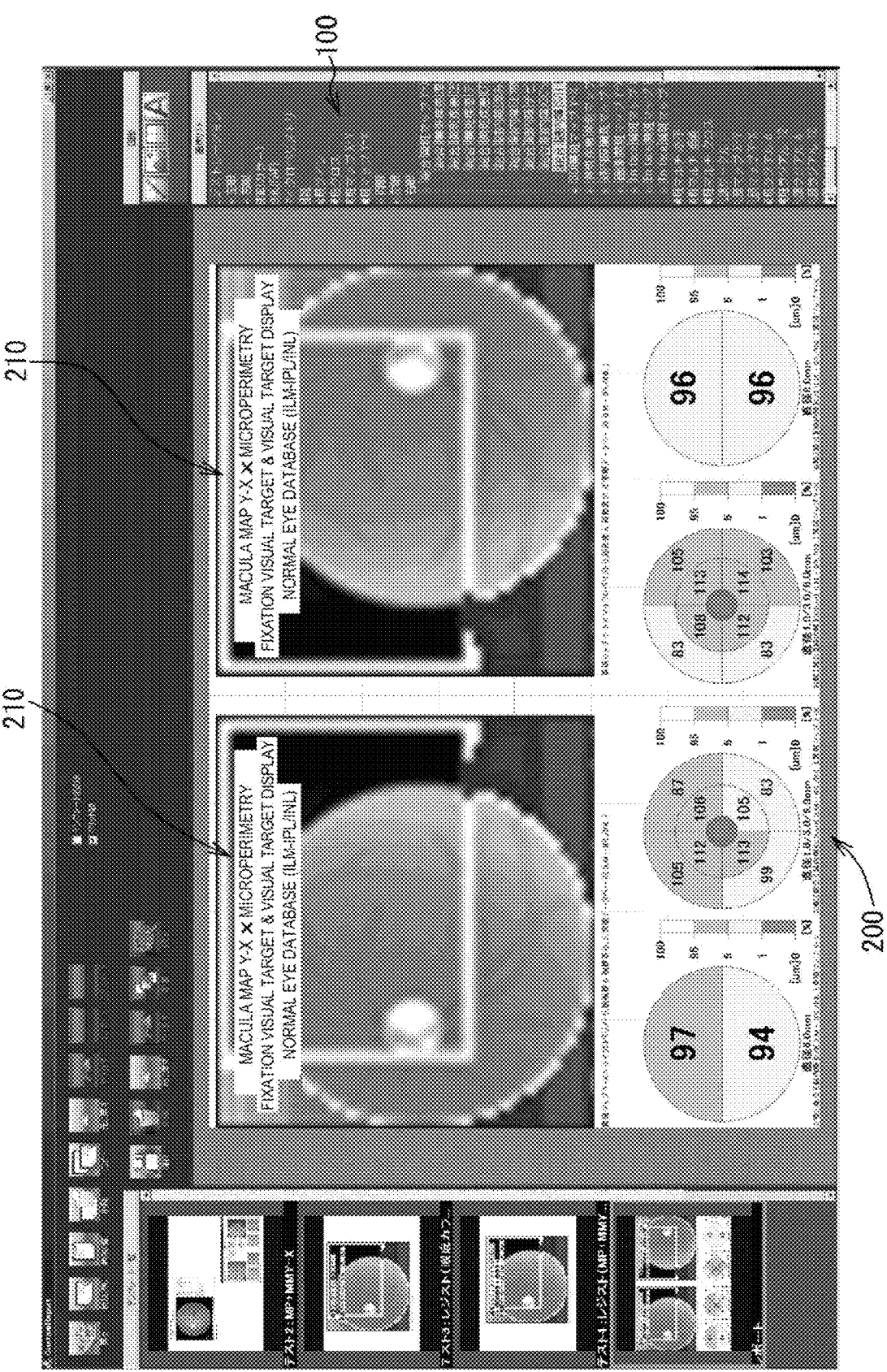
FIG. 8 is a diagram illustrating an example of a template generation screen.
Figure 9:
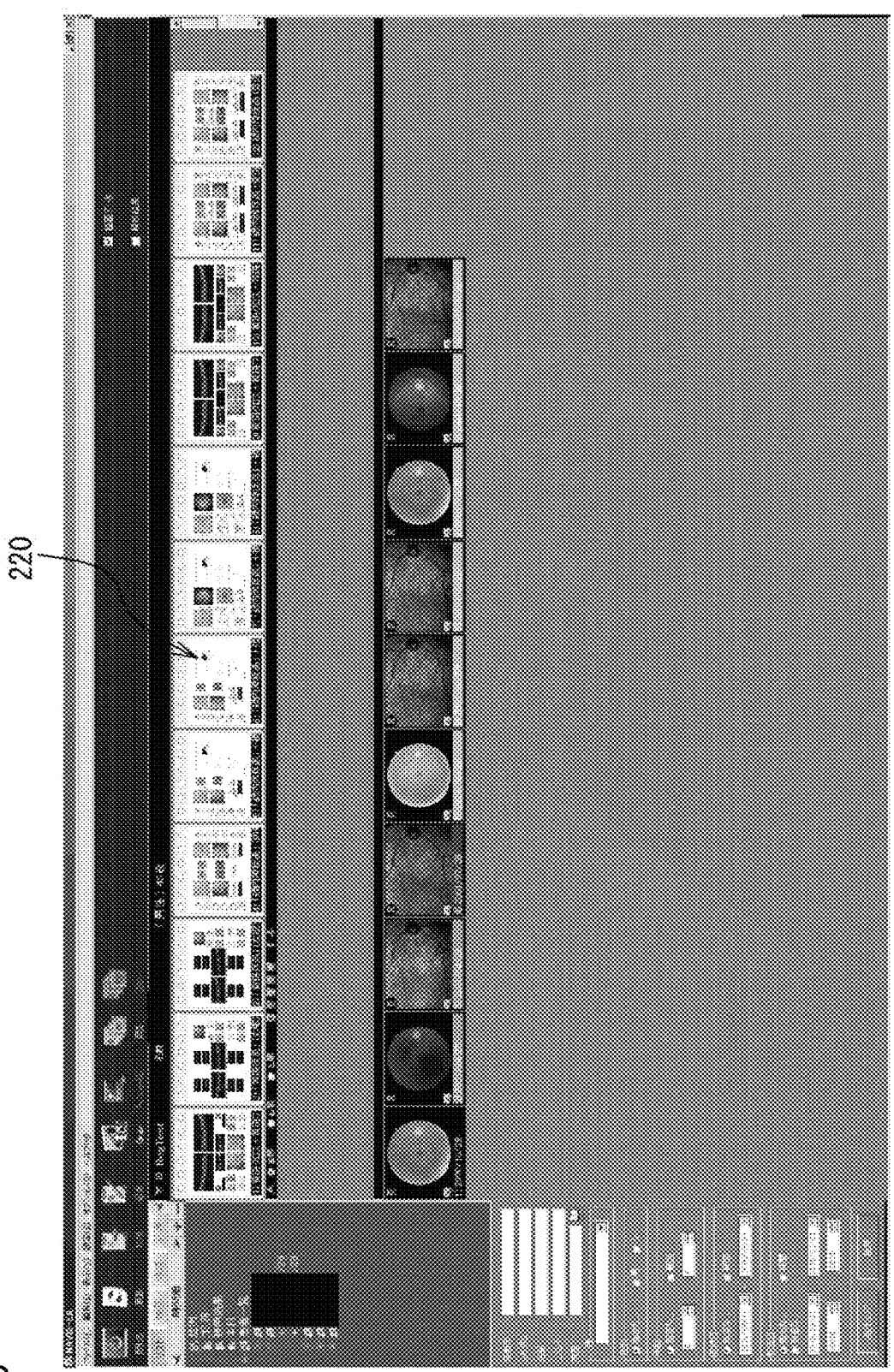
FIG. 9 is a diagram illustrating an example of a selection screen for selecting one of reports in this example.
Figure 10:
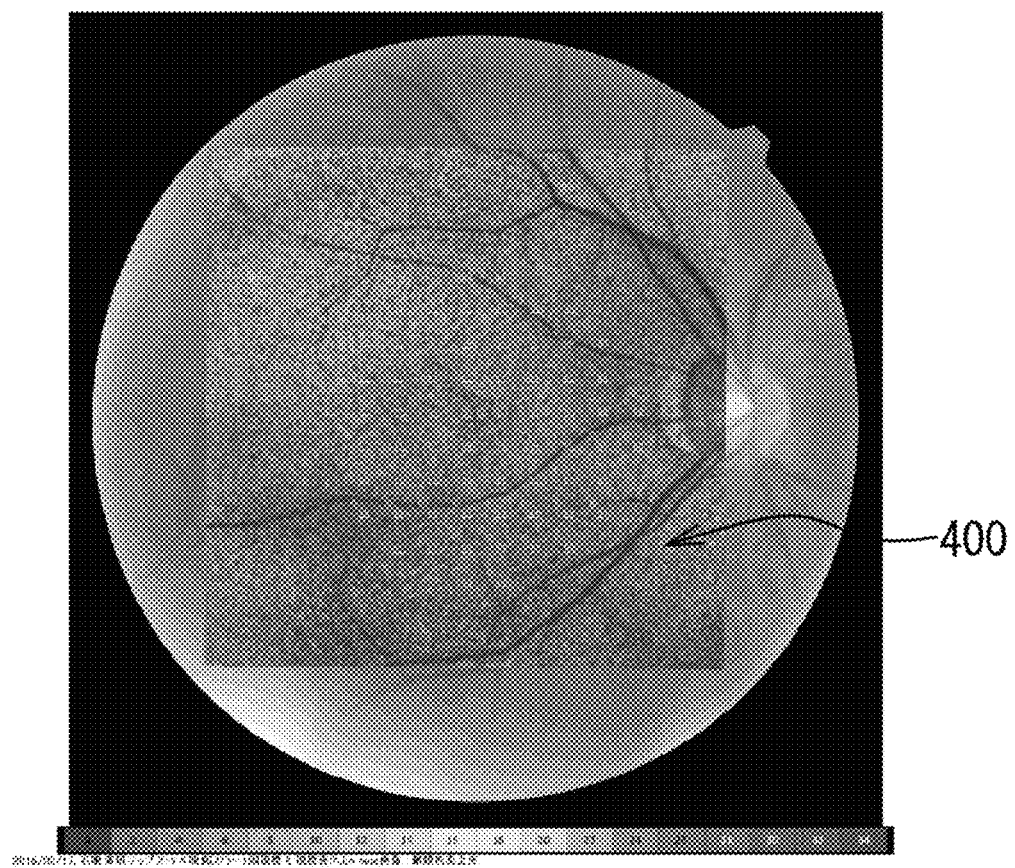
FIG. 10 is a diagram illustrating an example of a registration image according to this example.
Figure 11:
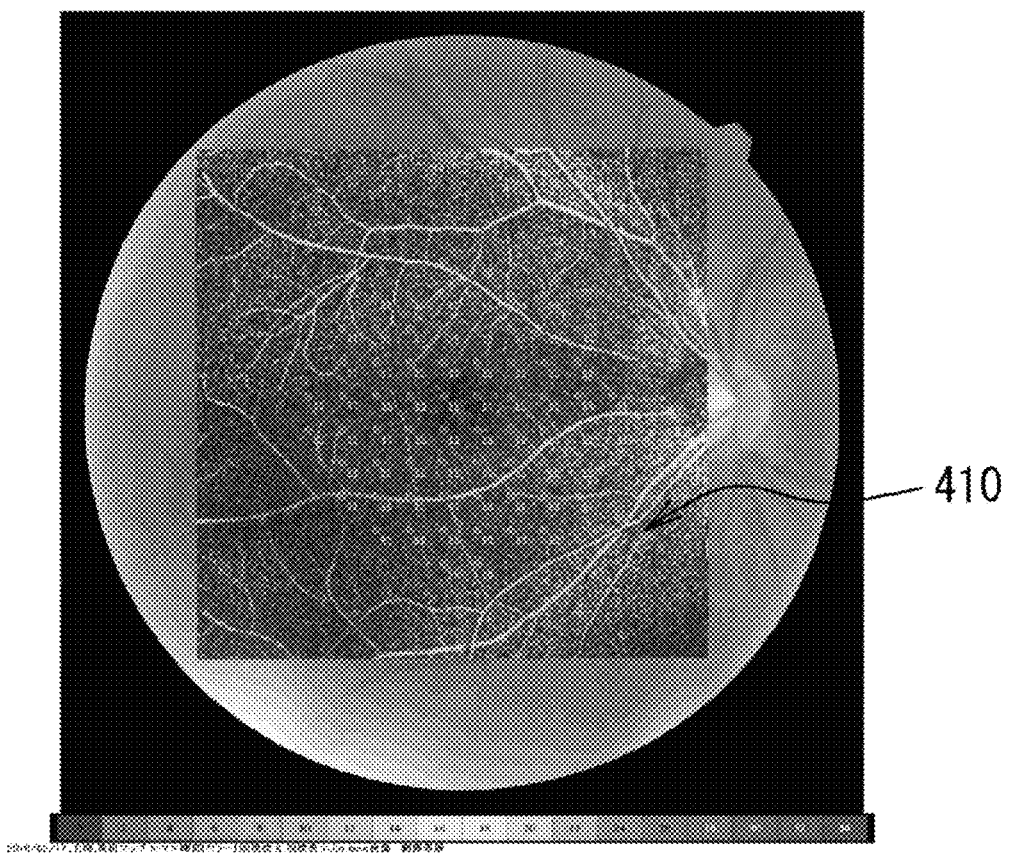
FIG. 11 is a diagram illustrating an example of a registration image according to this example.

FIG. 8 is a diagram illustrating an example of a screen for generating a template of a report on software. The processor 20 can generate a template of a report including a registration image. The report including the registration image may be a report using only one or a plurality of registration images, or may be a report (see FIG. 4) including another image acquired by the ophthalmic examination apparatus in addition to one or a plurality of registration images. Examples of another image to be considered include a two-dimensional image (for example, a map image, an OCT En face image, an analysis chart image, a front image, or the like) which is acquired by the ophthalmic OCT device, a two-dimensional image (for example, a map image or a front image) which is acquired by the visual field examination apparatus, a front image acquired by an eye photographing apparatus, and the like.

In the template generation screen, the processor 20 may selectably display a plurality of image types on the display unit and may receive a selection instruction from the operation unit 4 for selecting the image type. For example, the plurality of image types may be displayed as a list 100.

A registration image may be selected as a selectable image type. A plurality of image types of the registration image are provided, and one of the plurality of image types may be selectable. Various patterns of the image types of the registration image are considered (details thereof will be described later). In this case, selection methods may include a method of selecting one of the plurality of image types of the registration image, and a method of selecting an image type of the registration image by selecting a plurality of image types of images which are the bases of the registration image.

The registration image may be an image in which images acquired by different ophthalmic examination apparatuses are superimposed on each other. Examples of the images acquired by the different ophthalmic examination apparatuses may include images respectively acquired by the ophthalmic OCT device and another ophthalmic examination apparatus, and images respectively acquired by the visual field examination apparatus and another ophthalmic examination apparatus. Meanwhile, an image which is the basis of registration may be a captured image, a map image, or the like.

In the template generation screen, the processor 20 may receive an instruction signal for selecting an image type and may display an image corresponding to the selected image type in a report display region 200. In this case, at least one of the registration image and another image may be displayed in the report display region 200 in accordance with the selected image type.

The processor 20 may perform the addition or deletion (for example, a click operation, a drag operation, or the like) of an image type based on an operation signal received from the operation unit 4. The processor 20 may change an image to be displayed in the report display region 200 in accordance with the addition or deletion of an image type. The processor 20 may change a layout (for example, a display position, a display magnification, or the like) of each image displayed in the report display region 200 based on an operation signal received from the operation unit 4. In addition, in a case where a template is generated, the addition or deletion of an image type may be performed on a template including at least one image type in advance, or the addition or deletion of an image type may be performed on a new template.

In a case where an image type corresponding to the registration image is selected, the processor 20 may display an image 210 including at least one of characters and graphics indicating the type of registration image may be displayed in the report display region 200. Thereby, an examiner can easily confirm the type of registration image. Meanwhile, characters indicating the type of each image which is the basis of the registration image are displayed, and thus the examiner can reliably and smoothly confirm the type of registration image. In a case where graphics indicating the type of registration image are displayed, the graphics may be an actual captured image or may be a graphic image imitating an actual image.

When a template of a report is generated based on an image type displayed in the report display region 200, the generated template is stored in the storage unit 30. The generated template can be output as a report.

<Templet Selection Screen>

In the template selection screen (see FIG. 4), a selection instruction may be received from the operation unit 4 for selecting one of a plurality of templates. The processor 20 may display a plurality of templates 220 on the display unit 1 as graphics, and may receive a selection instruction from the operation unit 4. In this case, not only a default template but also a newly generated template may be displayed as the plurality of templates 220.

In this case, the processor 20 may receive a selection instruction from the operation unit 4 for selecting one subject from a plurality of pieces of subject information stored in the storage unit 30. When a template is selected, the processor 20 may acquire an image, being an image of the selected subject, which corresponds to an image type on the selected template from the storage unit 30, and may generate a report based on the acquired image.

<Registration Screen>

In a case where a registration image is included in the selected template, the processor 20 may display a registration screen (see FIG. 2) for performing registration on the display unit 1. Meanwhile, in a case where a registration image is not included, the processor 20 may proceed to the generation of a report.

In the registration screen, the processor 20 may perform the alignment or superimposition (overlapping) of images acquired by different ophthalmic examination apparatuses. The processor 20 may perform the alignment of a first image (for example, a captured image A) which is an image acquired by the first ophthalmic examination apparatus and a second image (for example, a captured image B) which is an image acquired by the second ophthalmic examination apparatus. Here, as a first image type which is an image type of the first image and a second image type which is an image type of the second image, types that are set in the registration image on the template are applied.

<Alignment Process>

In the alignment process, in a case where at least one of the first image and the second image is another image (for example, a map image obtained by the OCT or visual field examination apparatus) which is not a front image, the processor 20 may perform alignment by using a front image which is set in advance with respect to the another image. For example, in a case of a map image obtained by the ophthalmic examination apparatus, a front image associated with map image in advance may be used. The ophthalmic examination apparatus may have a function of storing the map image and the front image in the storage unit 30 in association with each other. Meanwhile, a case where both another image and a front image are included as images constituting a registration image is also applicable.

Meanwhile, in a case where both the first image and the second image are front images (for example, a color fundus front image acquired by a fundus camera and a fluorescent fundus front image acquired by an SLO), the alignment of the front images may be directly performed.

In the alignment process, the processor 20 may display the front images (see the captured image A and the captured image B) which are used for the alignment on the display unit 1, and/or may display a registration image (see a result image of FIG. 2) of the front images used for the alignment on the display unit 1. The front images used for the alignment may be used not only for the confirmation of an image for alignment but also for the setting of a feature point for alignment. The registration image may be used to confirm the alignment.

The processor 20 may perform alignment (matching process) by performing image processing of the front images. Various image processing methods (a method using various correlation functions, a method using Fourier transform, and a method based on the matching of feature points) can be used as a specific method of the alignment through image processing. Meanwhile, in the alignment process, at least one of parallel movement, rotational movement, and enlargement/reduction may be performed. In addition, unconformity between images due to a difference in imaging optical system may be corrected by transforming at least one of the front images.

The alignment may be performed by an automatic method, may be performed by a semi-automatic method including a manual method, or may be performed by a manual method. In a case of the semi-automatic method, a feature point (for example, a blood vessel branching point, a lesion part, or the like) which is common to the front images is designated by an examiner on the screen, and the processor 20 may perform alignment by using the designated feature point. In a case of the manual method, the processor 20 may perform alignment by moving one front image on the screen with respect to the other front image in accordance with the examiner's operation. Meanwhile, the readjustment of alignment may be performed by a semi-automatic method or a manual method through the results of the alignment.

<Superimposition Process>

When the alignment process is completed, the processor 20 may display a registration image (see the result image of FIG. 2) in which at least the first image and the second image are superimposed on each other, on the display unit 1 by using the results of the alignment. The completion of the alignment may be automatically or manually performed.

In a case where at least one of the front images for alignment is included as an image constituting the registration image in addition to another image which is not a front image, the processor 20 may display the registration image in which the another image and the front image are superimposed on each other.

For example, in a case where the first image type is a first map image 300 which is a map image obtained by the first ophthalmic examination apparatus (for example, the ophthalmic OCT device 10) and the second image type is a second map image 310 which is a map image obtained by the second ophthalmic examination apparatus (for example, the visual field examination apparatus 15), the processor 20 may perform alignment between a first front image 320 which is a front image associated with the first map image and a second front image 330 which is a front image associated with the second map image, and may display a registration image having at least one of the first front image 320 and the second front image 330 superimposed thereon on the display unit 1 (see FIG. 5) in addition to displaying the first map image 300 and the second map image 310 that are superimposed on each other. Meanwhile, the processor 20 may display an image in which only the first map image 300 and the second map image 310 are superimposed on each other by using the first front image 320 and the second front image 330 for the alignment.

The processor 20 may display a registration image in which front images for alignment are superimposed on each other. In this case, the superimposition image for alignment may also serve as a registration image.

Meanwhile, in a case where the first image type is a first front image which is a front image obtained by the first ophthalmic examination apparatus (for example, a fundus camera) and the second image type is a second front image which is a front image obtained by the second ophthalmic examination apparatus (for example, an SLO), the processor 20 may perform alignment between the first front image and the second front image and may display a registration image in which the first front image and the second front image are superimposed on each other, on the display unit 1.

<Order of Superimposition>

In the registration screen, the processor 20 may generate a registration image based on the order of superimposition which is set in advance, and may display the generated registration image on the display unit 1.

Regarding a superimposition order which is set in advance, an analysis-related image (for example, a map image) is superimposed at a position above a front image, thereby obtaining a registration image having analysis results given precedence. Thereby, it is possible to easily confirm a correspondence relationship between the analysis results on the front image.

For example, in a case where the first image type is a first map image and the second image type is a second map image, the processor 20 may display a registration image having the first map image and the second map image superimposed on each other at a position above the first front image and the second front image on the display unit 1.

Further, regarding the order in which the first front image and the second front image are superimposed on each other, the front image having a small angle of view is superimposed on the front image having a large imaging angle of view, and thus an examiner can confirm an imaging region in a wide range by the front image having a large imaging angle of view and to easily confirm a correspondence relationship between the front image having a small angle of view and the map image in the entire imaging region.

In addition, regarding the order in which the first map image and the second map image are superimposed on each other, a map image (for example, a map image of the visual field examination apparatus) which is discretely displayed is superimposed on a map image (for example, a map image of the OCT) which is exhaustively displayed in a two-dimensional manner, and thus an examiner can confirm analysis results based on the exhaustive map image in a wide range and to easily confirm a correspondence relationship between analysis results based on the exhaustive map image and the discrete map image with respect to the front image. For example, the map image of the visual field examination apparatus which is discretely displayed is superimposed on the map image of the OCT which is exhaustively displayed, and thus the examiner can confirm the analysis results of the OCT in a wide range and to easily confirm a correspondence relationship between the analysis results of the OCT and the analysis results of the visual field examination apparatus with respect to the front image. This is because the map image of the OCT is generally a color map which is two-dimensionally colored within a rectangular region, while the map image of the visual field examination apparatus is generally limited to a visual field measurement point, a fixation view point, and the like.

<Change of Setting of Registration Image>

Figure 3:
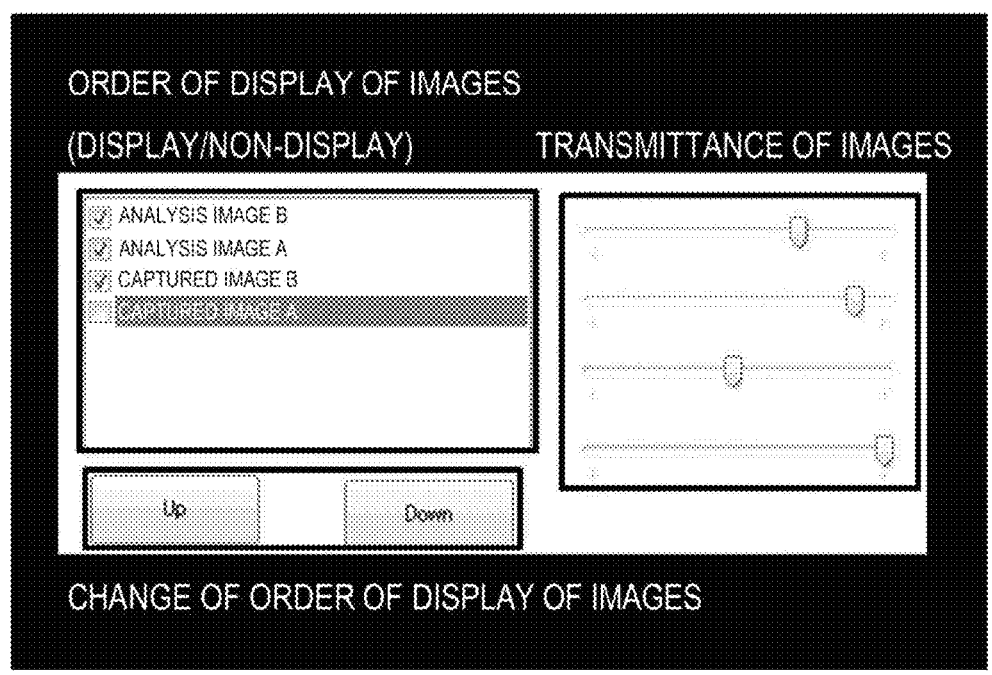
FIG. 3 is a diagram illustrating an example of a setting screen in the registration screen according to this example.

In the registration screen, the processor 20 may receive an instruction signal from the operation unit 4 for changing the setting of a registration image, may generate the registration image according to the changed setting, and may display the generated registration image on the display unit 1 (see FIG. 3).

In a case where the setting of the registration image is changed, the processor 20 may change the setting of the registration image which is set on a template and may store the changed setting in the storage unit 30. The setting of the registration image can be changed, and thus an examiner can perform a change to a desired registration image. In addition, the examiner can compositely confirm a correspondence relationship between images from registration images having different settings by appropriately changing the setting of the registration image, which brings an advantage in diagnosis.

Regarding the change of setting, for example, the processor 20 may receive an instruction signal from the operation unit 4 for changing the order of superimposition, may generate a registration image according to the changed order, and may display the generated registration image on the display unit 1. An examiner can change the order while viewing the registration image, and thus it is possible to easily perform a change to the examiner's desired registration image. For example, in a case where one of the first front image and the second front image is a color front image and the other is a fluorescent front image, the visibility of the front image displayed on the upper side is improved.

Accordingly, in a case where a lesion and the like are confirmed in the upper image and a correspondence relationship with the lower image with respect to the lesion and the like is confirmed by switching the order between the color front image and the fluorescent front image, it is possible to easily perform confirmation in both the images.

Regarding the change of setting, for example, the processor 20 may receive an instruction signal from the operation unit 4 for selecting the presence or absence of an image type to be applied to a registration image, may generate the registration image according to the changed image type, and may display the generated registration image on the display unit 1.

In this case, for example, image types applied to the registration image are displayed on the display unit 1, and the processor 20 may receive a switching signal for each image type from the operation unit 4 and may switch an image type to be applied to the registration image on the display unit 1 (see check boxes of FIG. 3). In a case where non-application is set with respect to one of the image types applied to the registration image, the processor 20 may delete the image related to the image type set to be non-application from the registration image on the display unit 1. On the other hand, the processor 20 may display the registration image based on the image type set to be application on the display unit 1.

Application to the registration image can be switched with respect to each image type, and thus it is possible to obtain the examiner's desired registration image and to more reliably confirm a correspondence relationship between images. For example, in a case where the map image in the first ophthalmic examination apparatus is deleted, it is possible to more directly confirm a correspondence relationship between the map image in the second ophthalmic examination apparatus and the front image.

Regarding the change of setting, for example, the processor 20 may receive an instruction signal from the operation unit 4 for changing the transmittance of an image applied to a registration image, may generate the registration image according to the changed transmittance, and may display the generated registration image on the display unit 1.

In this case, for example, a transmittance of each image type applied to the registration image is displayed on the display unit 1 so as to be changeable, and the processor 20 may receive a signal for changing the transmittance from the operation unit 4 and may change the transmittance of an image applied to the registration image on the display unit 1 (see a slider of FIG. 3).

A transmittance for the registration image can be changed with respect to each image type, and thus it is possible to obtain the examiner's desired registration image and to more reliably confirm a correspondence relationship between images. For example, in a case where the transmittance of a certain image is changed, display conditions between the images applied to the registration image are changed, and the relation between the images is changed. The examiner can acquire an image which is set to have the examiner's desired relation between the images by the change in the transmittance. For example, in a case where a first map image (for example, a map image of the visual field examination apparatus) is displayed on a second map image (for example, a map image of the OCT) and a front image is displayed below the map image, the transmittance of the second map image is increased, and thus the examiner easily confirms a correspondence relationship between the first map image and the front image.

<Display of Report>

In the registration screen, when the setting of a registration image is completed, the processor 20 may generate a report including the set registration image. Meanwhile, in a case where a template does not include the registration image, the processor 20 may omit the registration screen.

Figure 4:
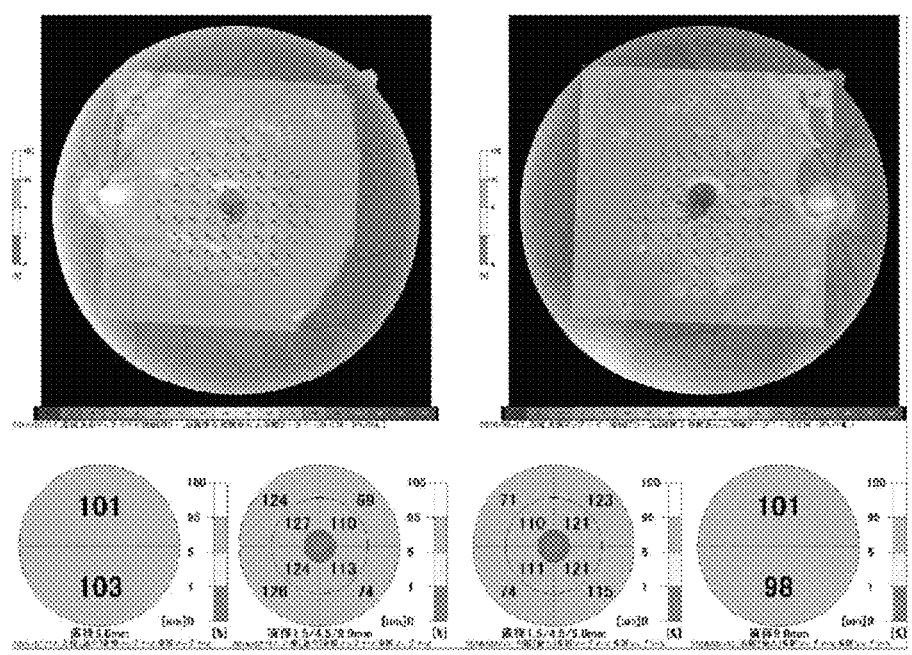
FIG. 4 is a diagram illustrating an example of a report according to this example.

The processor 20 may display the generated report on the display unit 1, may store the report in the storage unit 30, may output the report to the outside, or may print the report (see FIG. 4). Here, the registration image included in the report is a registration image selected by an examiner from a plurality of types of registration images, and thus the examiner can perform the examiner's desired diagnosis by using the registration image and another image.

<Generation and Output of Report Based on Examination Date>

Figure 7:
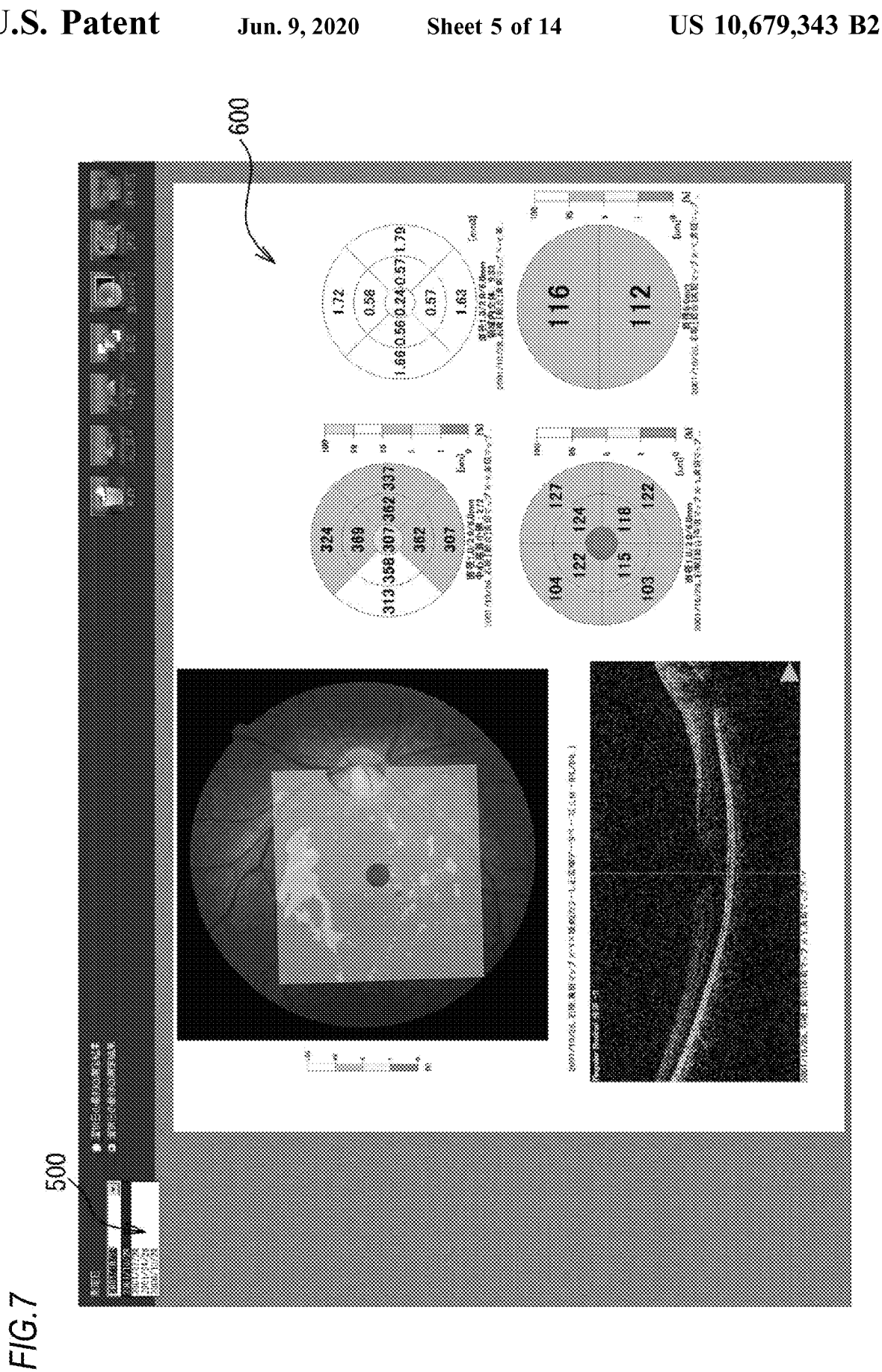
FIG. 7 is a diagram illustrating an example of a screen for outputting a report based on an examination date according to this example.

In the generation and output of a report, the processor 20 may receive an instruction for selecting an examination date from the operation unit 4, and may generate a report based on an image on the selected examination date or within a predetermined period of time based on the examination date (see FIG. 7). Meanwhile, the range of the predetermined period of time may be selectable by an examiner. In addition, it is assumed that the examination date includes a display mode as represented by an examination month.

Here, an image is managed by the examination date, and thus it is possible to easily display data of the examiner's desired examination date. In addition, it is also possible to perform follow-up observation by changing the examination date. Meanwhile, in a case where a plurality of examination dates are simultaneously designated, the processor 20 may output a report in which images having different examination dates are output over time, as a report for follow-up observation.

In addition, on the same screen as the report output screen, an examination date can be selected, and thus it is possible to easily output a report having the examiner's desired examination date and to easily confirm the contents of the report. It is possible to smoothly perform follow-up observation by the change of the examination date. In this case, the processor 20 may update the output contents of the report in accordance with the selected examination date.

Meanwhile, the examination date may be automatically selected, in addition to being selected by the examiner. For example, an examination date on which an abnormality is observed in analysis results may be automatically selected and may be output as a report.

Figure 13:
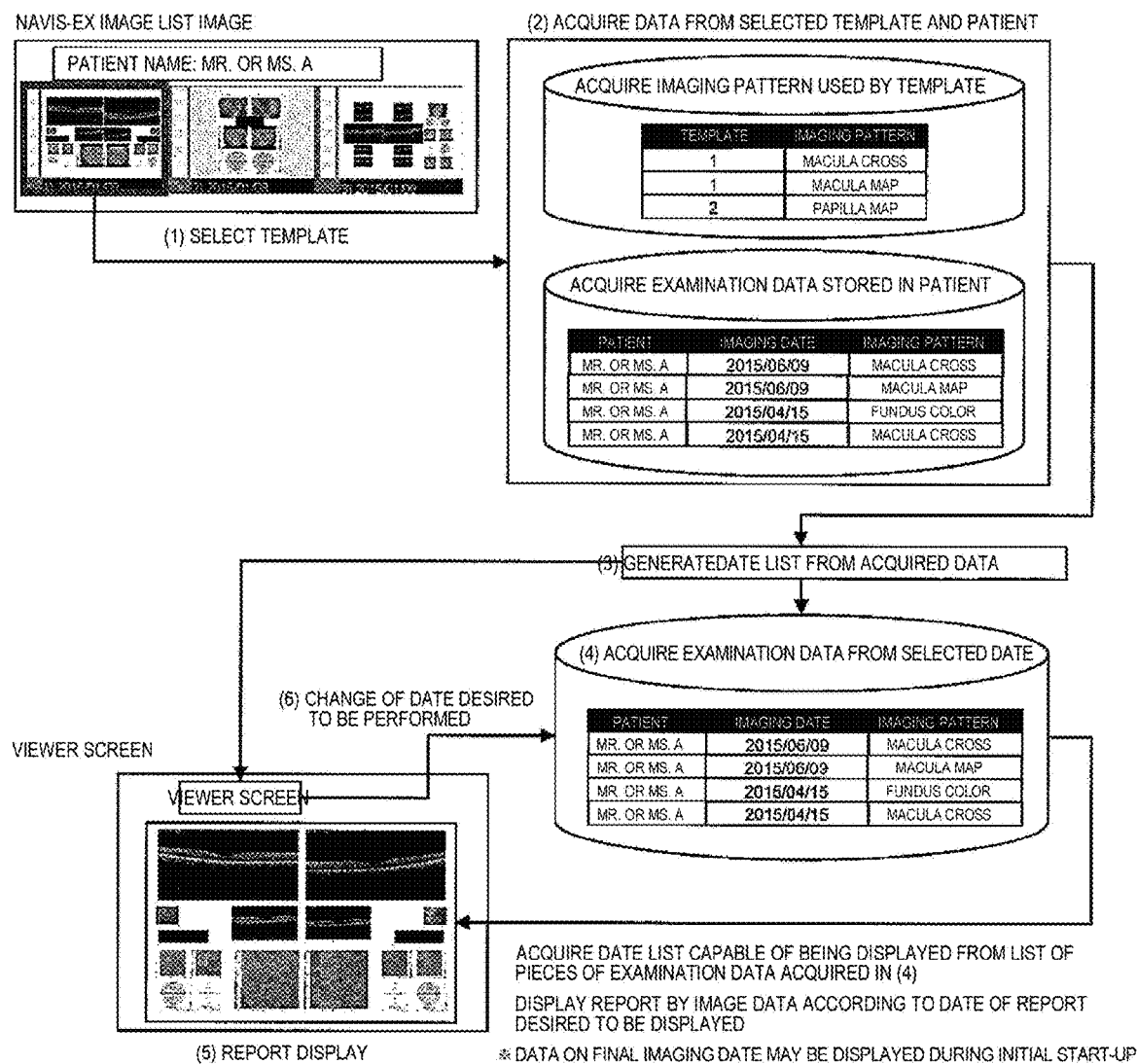
FIG. 13 is a diagram illustrating an example of a screen for outputting image data based on an examination date according to this example.

FIGS. 7 and 13 are diagrams illustrating a specific example when a report according to an examination date is output. The processor 20 may receive an instruction for selecting one template from templates of a plurality of reports displayed and may select a template. Meanwhile, the template may be generated in advance by an examiner. For example, a template constituted by scanning patterns (for example, a "macula cross" and a "macula map") during the measurement of a specific imaging region may be generated. The generated template may be displayed on an image list screen on the display unit 1.

When the template is selected, the processor 20 may acquire an image corresponding to an image type which is set as a template, from images of a subject which are stored in the storage unit 30. The processor 20 may generate an examination date list 500 from the acquired examination data (see FIG. 7). The generated examination date list is displayed on the display unit 1. In more detail, a list of examination dates appropriate for the template may be generated from captured images corresponding to a scanning pattern included in the template and a scanning pattern stored in the storage unit 30.

When an examination date is selected from the examination date list, the processor 20 may acquire an image corresponding to the selected examination date (for example, a date and a time) from the storage unit 30, and may generate a report 600 by using the acquired image. In a case where the examination date is changed from the generated examination date list after the report is displayed, the processor 20 may acquire an image corresponding to the changed examination date and may update the contents of the report.

In this case, an image according to the selected examination date is displayed as a report. Meanwhile, data on a final imaging date (latest data) may be displayed during the initial start-up. These processes are performed by the processor 20 based on an operation signal received from the operation unit 4.

<Pattern of Image Type of Registration Image>

Hereinafter, specific examples of various patterns in a registration image will be described. Examples of respective patterns to be described below may be selectable as a plurality of image types in a registration image. The patterns are just examples, and it is natural that this disclosure is not limited thereto.

A first example of a registration image may be, for example, a registration image in which an OCT two-dimensional image (for example, an OCT map image, an En face OCT image, or the like) which is acquired by the ophthalmic OCT device and a map image acquired by the visual field examination apparatus are superimposed on each other (see FIG. 5).

A second example of a registration image may be, for example, a registration image in which a two-dimensional image (for example, a map image, an OCT En face image, or the like) which is acquired by the ophthalmic OCT device and a captured image or a map image which is acquired by another ophthalmic examination apparatus different from the visual field examination apparatus are superimposed on each other.

Figure 6:
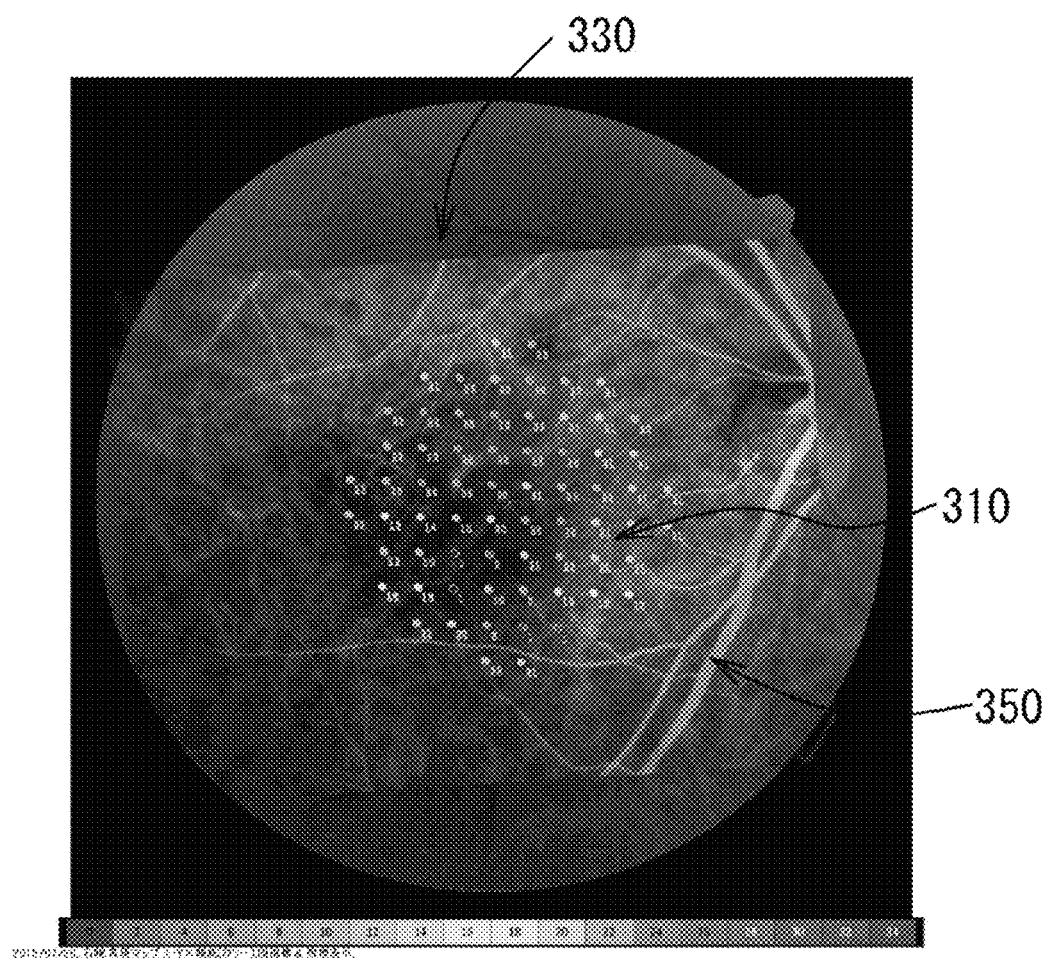
FIG. 6 is a diagram illustrating an example of a registration image according to this example.

A third example of a registration image may be, for example, a registration image in which a map image acquired by the visual field examination apparatus and a captured image or a map image which is acquired by another ophthalmic examination apparatus different from the visual field examination apparatus are superimposed on each other (see FIG. 6).

Meanwhile, the ophthalmic OCT device may be a fundus OCT capable of acquiring a two-dimensional image of a fundus. In addition, the eye photographing apparatus may be a fundus imaging apparatus. Thereby, it is possible to acquire a registration image related to the image of the fundus. In addition, a registration image may be generated using the two-dimensional image of the fundus obtained by the fundus OCT or the fundus image obtained by the fundus imaging apparatus, and the map image obtained by the visual field examination apparatus. Meanwhile, this embodiment is not limited to the fundus, and can also be applied to an image related to an anterior ocular segment or an image related to an eyeball including an anterior ocular segment and a fundus.

<OCT Map Image>

An OCT map image constituting a registration image may be image data of a so-called analysis map. For example, the map image is image data which is obtained by analyzing OCT data obtained by the OCT optical system provided in the ophthalmic OCT device, and may be displayed on the display unit 1 as an analysis map image.

For example, the OCT map image may be an analysis map image indicating a two-dimensional distribution of measurement results related to a subject eye (for example, a fundus). In this case, the OCT map image may be, for example, a color map color-coded in accordance with a measurement value. The analysis map may be, for example, a thickness map indicating a layer thickness, a comparison map (normal eye DB map) indicating results of comparison between the layer thickness of the subject eye and the layer thickness of a normal eye which is stored in a normal eye database, or a deviation map indicating a deviation between the layer thickness of the subject eye and the layer thickness of the normal eye which is stored in the normal eye database by a standard deviation. Meanwhile, in a case where the layer thickness is obtained, for example, OCT data is subjected to division processing for each layer by image processing (for example, segmentation processing) for the OCT data, and the thickness of each layer is measured based on an interval between layer boundaries.

The analysis map is not limited to the layer thickness, and may be, for example, a map indicating a curvature distribution or may be a map indicating a blood vessel density distribution. For example, the map indicating a blood vessel density distribution may be acquired by analyzing OCT motion contrast data. In addition, the analysis map may be a map indicating a polarization characteristic distribution obtained by a polarization sensitive OCT (PS-OCT). The analysis map may be a map indicating a blood flow velocity distribution obtained by a doppler OCT.

Figure 12:
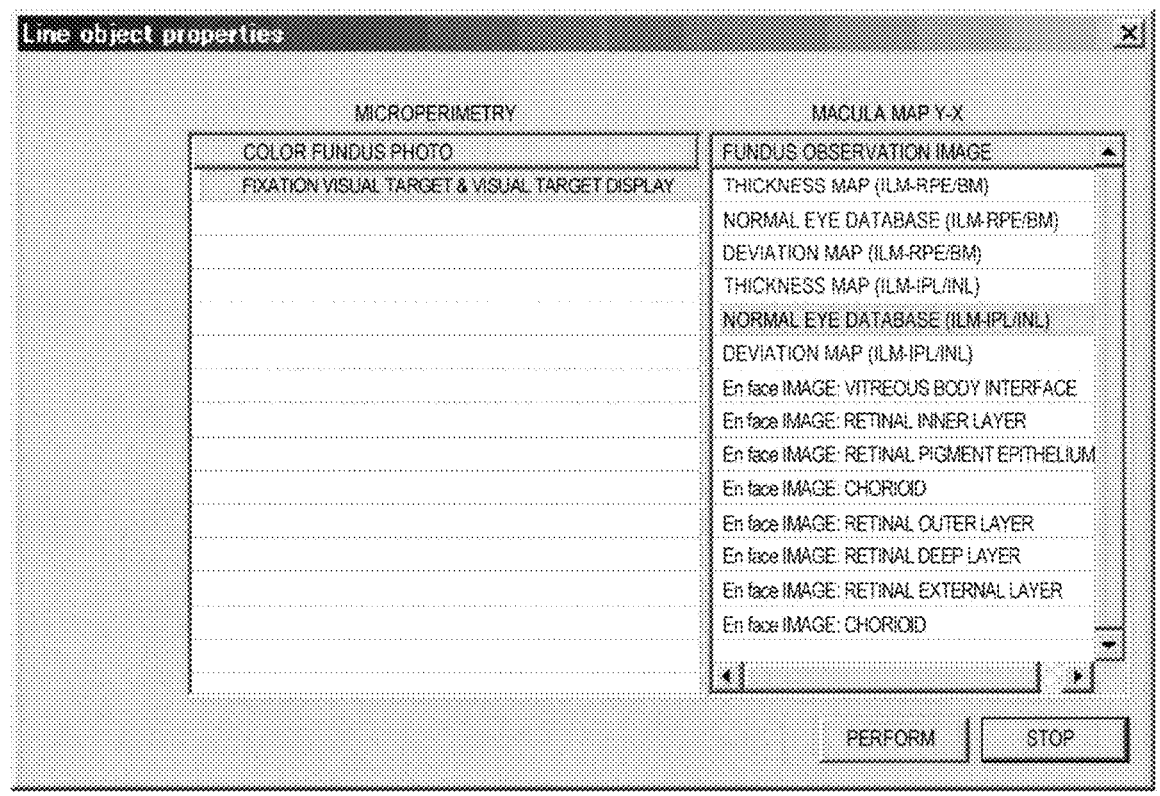
FIG. 12 is a diagram illustrating an example of a selection screen for selecting an OCT two-dimensional image according to this example.

The processor 20 may selectably display a plurality of image types related to an OCT map image as image types constituting a registration image (see FIG. 12). For example, the processor 20 may selectably display the thickness map, the normal eye DB map, and the deviation map. In this case, regarding the maps, it may be possible to select maps related to different layer regions. In addition, the thickness map, the normal eye DB map, and the deviation map may be acquired from the storage unit 30, a registration image may be generated for each map, and each registration image may be displayed on the display unit 1. Thereby, it is possible to simultaneously confirm the registration images related to the respective map images.

For example, the processor 20 generates a registration image in which an OCT map image related to a specific layer region and a map image acquired by the visual field examination apparatus are superimposed on each other, and thus an examiner can confirm a correspondence relationship between an analysis result of a specific retina layer and a visual field.

<OCT En-Face Image>

An OCT En face image which is the basis of a registration image may be an OCT signal front image generated from an OCT signal obtained by the OCT optical system, may be a front image generated from three-dimensional OCT data, or may be a front image generated from an interference signal which is the basis of OCT data. Meanwhile, the three-dimensional OCT data may be acquired by raster scanning.

In addition, an OCT En face image which is the basis of a registration image may be an OCT motion contrast front image (OCT motion contrast En face image; hereinafter, motion contrast will be simply referred to as MC) which is generated from an OCT motion contrast signal obtained by the OCT optical system, or may be an OCT MC front image generated from three-dimensional OCT MC data. The MC data is acquired based on a plurality of pieces of OCT data that are temporally different from each other with respect to the same position. Examples of a method of computationally calculating OCT data for acquiring the MC data include a method of calculating a difference in intensity or a difference in amplitude of complex OCT data, a method of calculating a distribution of intensities or amplitudes of complex OCT data or a standard deviation (Speckle variance), a method of calculating a phase difference or a distribution of complex OCT data, a method of calculating a vector difference of complex OCT data, and a method of multiplying a phase difference and a vector difference of a complex OCT signal. Meanwhile, as one of computational calculation methods, for example, JP-A-2015-131107 is referred to. The three-dimensional OCT MC data may be acquired by pieces of motion contrast data in different scanning lines being arranged. Meanwhile, as described above, the motion contrast data is not limited to the phase difference, and a difference in intensity, a vector difference, and the like may be acquired.

For example, the front image generated from the above-described three-dimensional OCT data (or three-dimensional OCT MC data) may be acquired by imaging three-dimensional OCT data with respect to at least a portion of a region in the depth direction. In more detail, the OCT En face image may be acquired by computationally calculating three-dimensional OCT data (or three-dimensional OCT MC data) with respect to the entire region in the depth direction. The OCT En face image may be acquired by computationally calculating three-dimensional OCT data (or three-dimensional OCT MC data) with respect to a portion of a region (for example, a specific layer region or a specific depth region) in the depth direction. The computational calculation method may be integration processing, or may be another method (for example, histogram calculation).

The processor 20 may selectably display a plurality of image types related to an OCT En face image, as image types constituting a registration image. For example, the En face images may be classified according to different depth regions (for example, different layer regions in the depth direction), and the En face images classified according to the depth regions may be selectably displayed. In addition, the En face images having different depth regions may be acquired from the storage unit 30, a registration image may be generated for each En face image, and each registration image may be displayed on the display unit 1. Thereby, it is possible to simultaneously confirm the registration images related to the respective En face images having different depth regions. In addition, it may be possible to perform selection between the OCT signal front image and the OCT motion contrast front image.

For example, the processor 20 generates a registration image in which an OCT En face image related to a specific layer region and a map image acquired by the visual field examination apparatus are superimposed on each other, and thus an examiner can confirm a correspondence relationship between a specific retina layer structure and a visual field. In this case, setting to a registration image of an OCT front image in the specific layer region and the map image of the visual field examination apparatus is performed, and thus it is possible to confirm a correspondence relationship between form information in specific layer and a visual field.

In this case, a registration image (see FIG. 10) in which an OCT En face image (in FIG. 10, an OCT signal front image) 400 related to a specific layer region and a map image acquired by the visual field examination apparatus are superimposed on each other is generated, and thus an examiner can confirm a correspondence relationship between a specific retina layer structure and a visual field. For example, the examiner can confirm a defective region from a front image related to an RPE layer and can collate the defective region with visual field measurement results to thereby easily confirm a relation therebetween.

In addition, a registration image (see FIG. 11) in which an OCT MC front image 410 and a map image acquired by the visual field examination apparatus are superimposed on each other is generated, and thus the examiner can confirm a correspondence relationship between blood vessel information and a visual field. For example, the examiner can easily confirm a traveling state of a blood vessel with respect to a FAZ region and visual field measurement results in the FAZ region in association with each other.

<Method of Classifying OCT Two-Dimensional Images>

OCT two-dimensional images (for example, OCT map images, OCT En face images, or the like) which constitutes a registration image may be classified according to imaging regions, and one of the plurality of OCT two-dimensional images classified according to imaging regions may be selectable as an image type constituting the registration image. For example, an OCT two-dimensional image of a macula and an OCT two-dimensional image of a papilla may be selectable as image types.

The OCT two-dimensional image may be an X-Y image in which the horizontal axis and the vertical axis are respectively set to be an X-axis and a Y-axis, may be a Y-X image in which the horizontal axis and the vertical axis are respectively set to be a Y-axis and an X-axis, or may be configured such that a relationship between vertical and horizontal axes of the image is selectable. Here, an X-axis direction is specified as a horizontal direction perpendicular to the depth direction, and a Y-axis direction is specified as a vertical direction perpendicular to the depth direction.

Meanwhile, in a case where the OCT two-dimensional images are map images, the map images may be classified according to scanning patterns, or one of the plurality of map images classified according to the scanning patterns may be selectable. For example, the map image is acquired based on OCT data acquired by raster scanning and OCT data acquired by radial scanning. Consequently, the map image based on the raster scanning and the map image based on the radial scanning may be selectable as image types constituting the registration image.

In addition, the OCT two-dimensional images may be classified according to types of ophthalmic OCT devices, and one of the plurality of OCT two-dimensional images classified according to the types of devices may be selectable as an image type constituting the registration image.

For example, the ophthalmic OCT device may be a composite machine of an OCT and an SLO, a composite machine of an OCT and a fundus camera, or an OCT single device, and thus at least two of the devices may be selectable as image types (classification based on a front imaging system). In addition, for example, the ophthalmic OCT device may be an SD-OCT, an SS-OCT, or a TD-OCT, and thus at least two of the devices may be selectable as image types (classification based on an OCT principal). Meanwhile, in a case of classification according to device types, classifications based on the front imaging system and the OCT principal may be configured as a set.

Meanwhile, as described above, the OCT two-dimensional images are classified according to imaging regions, a horizontal-vertical axis relationship, scanning patterns, imaging apparatuses, which brings convenience in generating an examiner's desired registration image.

Meanwhile, in the example of FIG. 8, types of OCT two-dimensional images constituting a registration image are classified in at least units of imaging regions (see the list 100). When the imaging region is selected, the type of map image or an OCT En face image is further selectable (see FIG. 12).

<Front Image Associated with OCT Two-Dimensional Image>

A front image associated with an OCT two-dimensional image may be an image obtained by the OCT optical system provided in the ophthalmic OCT device or may be an image obtained by another front imaging optical system provided in the ophthalmic OCT device, and may be used for alignment between the front image and a front image acquired another ophthalmic examination apparatus. In addition, the front image associated with the OCT two-dimensional image may constitute a registration image together with the OCT two-dimensional image.

Meanwhile, a front image to be associated may be selectable between the image obtained by the OCT optical system and the image obtained by the front imaging optical system. The image obtained by the OCT optical system may be any of the above-described En face images. That is, in a case where the OCT two-dimensional image is an En face image, the OCT two-dimensional image may be used for alignment between the image and a front image acquired by another ophthalmic examination apparatus.

The front imaging optical system may be, for example, an SLO optical system or a fundus camera optical system. The front image obtained by the front imaging optical system may be a visible front image captured using visible light, an infrared front image captured using infrared light, or a fluorescent front image acquired by fluorescent imaging. The front images may be classified according to imaging wavelengths, and one of the plurality of front images classified according to imaging wavelengths may be selectable.

<Map Image of Visual Field Examination Apparatus>

A map image (hereinafter, a visual field map image) of the visual field examination apparatus which constitutes a registration image may be image data indicating analysis results obtained by visual field examination, or may be displayed on the display unit 1 as a visual field analysis map image.

The visual field map image may be a visual field analysis map image indicating a two-dimensional distribution of visual field measurement results related to a subject eye. The visual field analysis map may be a visibility map in which measurement values (for example, visibilities) at a plurality of visual field measurement points are two-dimensionally displayed, or may be a color map which is color-coded in accordance with measurement values (for example, visibilities) at a plurality of visual field measurement points. In this case, the color map may be a visibility (corresponding to the color of a sensitivity scale) color map in which complementation between visual targets is performed. In addition, the visual field analysis map may be a map related to a fixation view test. For example, the visual field analysis map may be a map indicating a fixation view stability obtained from a distribution of fixation view points at a central fovea, or may be a map indicating the positions of fixation view points. Meanwhile, the visual field examination apparatus may be a micro-perimeter, or may be a Humphrey perimeter.

Figure 16:
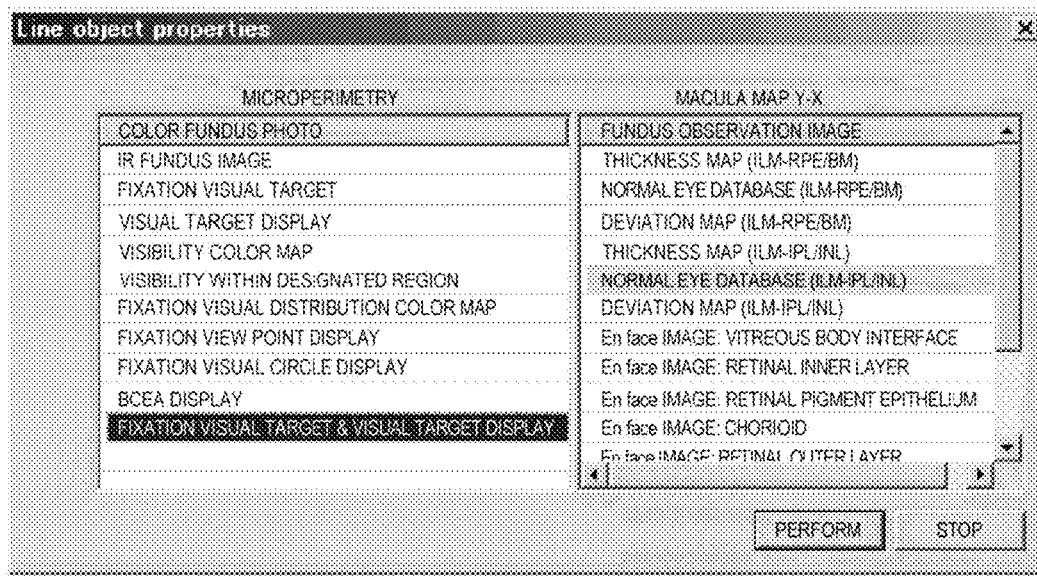
FIG. 16 is a diagram illustrating an example of a selection screen for selecting a map image of a perimeter according to this example.

The processor 20 may selectably display a plurality of image types related to the visual field map image, as image types constituting a registration image (see FIG. 16). For example, the processor 20 may selectably display the visibility map, the color map, the map related to a fixation view test, and the like. The type of visual field map image can be selected, and thus an examiner can multilaterally confirm OCT analysis results and visual field analysis results.

Meanwhile, a front image associated with the visual field map image may be an image obtained by a fundus front imaging optical system provided in the visual field examination apparatus. As the front imaging optical system, for example, a fundus camera optical system and an SLO optical system are considered. The front image obtained by the front imaging optical system may be a visible front image captured using visible light, an infrared front image captured using infrared light, or a fluorescent front image acquired by fluorescent imaging. The front images may be classified according to imaging wavelengths, and one of the plurality of front images classified according to imaging wavelengths may be selectable.

Meanwhile, in a case where a report including a registration image, having an OCT two-dimensional image and a map image of the visual field examination apparatus being superimposed on each other, and another image is generated, the processor 20 may generate the report including another image, corresponding to an imaging region, which is output as the registration image. In this case, such a report may be generated as a default template in advance.

The another image may be a map image or an En face image which is different from the OCT two-dimensional image constituting the registration image in addition to being, for example, a B scanning OCT image, a three-dimensional OCT image, an analysis chart, or an analysis graph. The processor 20 may generate a report including the original image of at least one of the OCT two-dimensional image constituting the registration image and a front image associated with the OCT two-dimensional image may be generated as another image.

<Third Ophthalmic Examination Apparatus Different from Ophthalmic OCT Device and Visual Field Examination Apparatus>

The third ophthalmic examination apparatus (another ophthalmic examination apparatus) may be, for example, an ophthalmic imaging apparatus (for example, the fundus imaging apparatus 17) for capturing an image of a subject eye (for example, a fundus), and a captured image acquired by the ophthalmic imaging apparatus may be selectable as an image type constituting a registration image. The fundus imaging apparatus may be, for example, a single fundus imaging apparatus for capturing a front image such as a fundus camera or an SLO. The ophthalmic imaging apparatus may be a stationary type apparatus or a handheld type apparatus.

The processor 20 may generate a registration image in which a third fundus front image 350 acquired by the fundus imaging apparatus 17, the map image 310 acquired by the visual field examination apparatus 15, and the second front image 330 associated with the map image 310 are superimposed on each other (see FIG. 6).

A front image obtained by the eye photographing apparatus may be a visible front image captured using visible light, an infrared front image captured using infrared light, or a fluorescent front image acquired by fluorescent imaging. The front images may be classified according to imaging wavelengths, and one of the plurality of front images classified according to imaging wavelengths may be selectable.

Another ophthalmic examination apparatus may be, for example, an ophthalmic blood flow velocity measurement apparatus (for example, a fundus blood flow measurement apparatus) for measuring a blood flow velocity of a subject eye, and a blood flow map image acquired by the ophthalmic blood flow velocity measurement apparatus may be selectable as an image type constituting a registration image. The blood flow map image may be, for example, a blood flow map image indicating a two-dimensional distribution of measurement results related to a blood flow velocity of an eye, or may be a color map color-coded in accordance with a measurement value. Meanwhile, the ophthalmic blood flow velocity measurement apparatus may be, for example, a blood flow velocity measurement apparatus (laser speckle flowgraphy: LSFG) for measuring a blood flow velocity based on a speckle signal reflected from blood cells of the eye (for example, JP-A-2003-180641).

In this case, a registration image of the blood flow map image and the OCT two-dimensional image is set, and thus an examiner can confirm a correspondence relationship between the OCT and the blood flow velocity. In addition, a registration image of the blood flow map image and a visual field map image is set, and thus it is possible to confirm a correspondence relationship between visual field measurement results and the blood flow velocity.

<Modification Example>

Meanwhile, in the above description, a configuration is adopted in which a registration image is provided in a template of a report, but this disclosure is not limited thereto. This embodiment can be applied in a case where a registration image is generated based on images obtained by a plurality of different ophthalmic examination apparatuses.

Meanwhile, in the above description, a description is given of an example in which a registration image is generated based on images obtained by a plurality of different ophthalmic examination apparatuses, but this embodiment may also be applied in a case where a registration image is generated between images obtained by a composite apparatus having a plurality of functions (for example, a composite machine of an OCT and a visual field examination apparatus).

<Enlargement of Image of Report>

Figure 17:
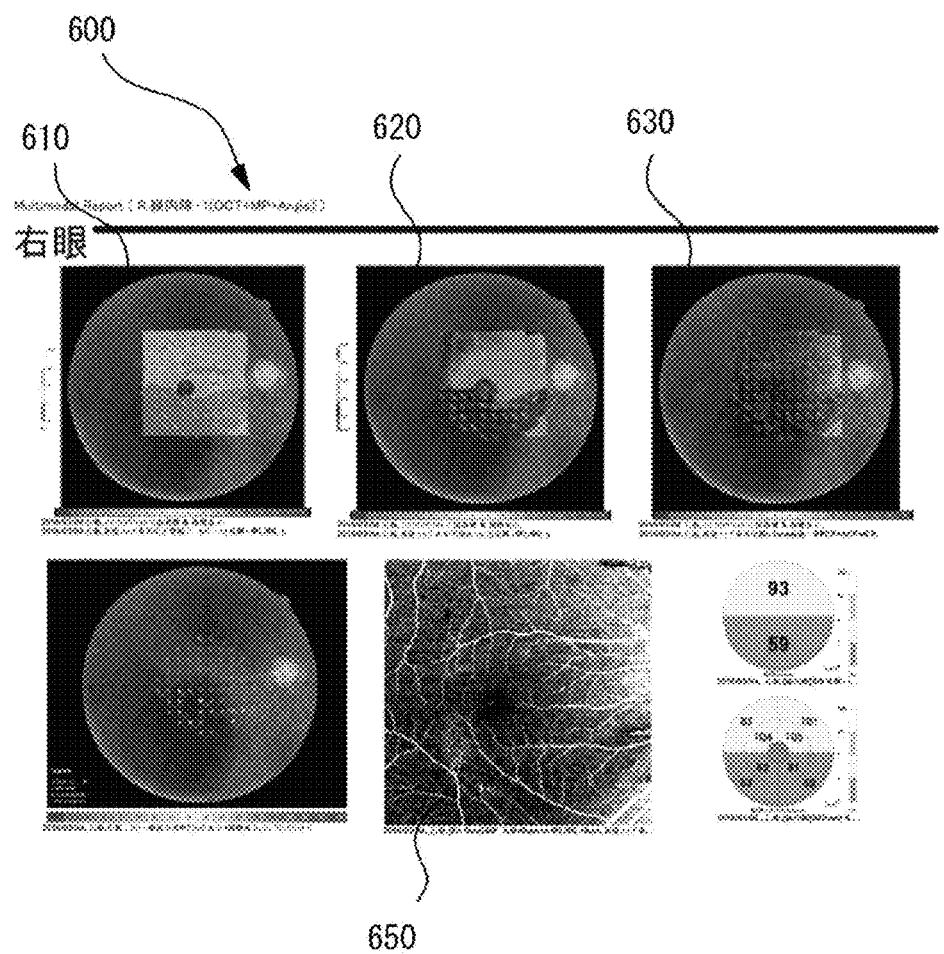
FIG. 17 illustrates an example of a report output screen.
Figure 18:
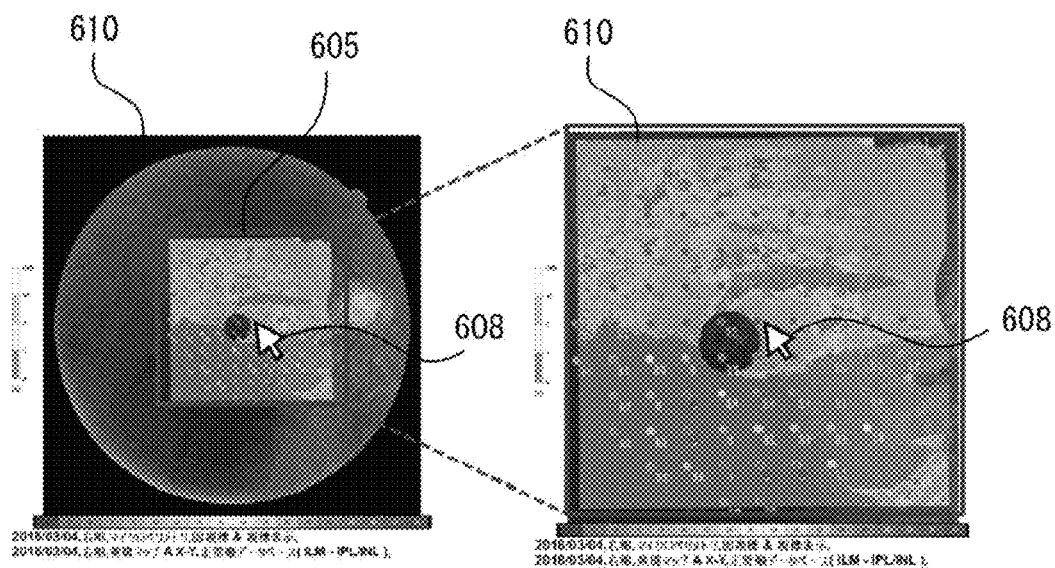
FIG. 18 illustrates an example of an image displayed on a report.

FIG. 17 illustrates an example of the report 600. The above-described registration image and the like are displayed on the report 600. One or a plurality of pieces of image data are displayed on the report 600. Regarding six pieces of image data of the report 600 illustrated in FIG. 17, all of the pieces of image data acquired by the ophthalmic examination apparatus are displayed. In a case where the image data displayed on the report 600 is enlarged, for example, an examiner selects image data desired to be enlarged. FIG. 18 illustrates an example of image data displayed on the report 600. For example, in a case where a mouse is used as an instruction reception unit, the examiner places a mouse cursor 608, displayed on the screen, on a portion of the image data which is desired to be enlarged, and rotates a mouse wheel in this state. The processor 20 performs enlargement or reduction of a portion of a region (also referred to as an enlarged region) of an image centering on the position of the mouse cursor 608, in accordance with the rotation direction of the mouse wheel. As illustrated in FIG. 18, the processor 20 can switch a state where the entire image data is displayed (left image of FIG. 18) to a state where an enlarged region 605 is displayed in an enlarged manner (right image of FIG. 18).

In a case where the mouse wheel is rotated upward, for example, the processor 20 gradually increases an enlargement rate for each scrolling centering on the mouse cursor 608. For example, the processor 20 may enlarge the image by 10% for each scrolling. In contrast, the processor 20 may reduce an enlargement rate in a case where the mouse wheel is rotated downward. Naturally, the range of fluctuation in the enlargement rate for each scrolling is not limited to 10%. The range of fluctuation may be 1% or 100%, or may be set to any value. In addition, it may be possible to change the range of fluctuation. For example, it may be possible to change the range of fluctuation in the enlargement rate for each scrolling from 10% to 20%. For example, in a case where scrolling is performed while pressing a Ctrl key of a keyboard, the image may be enlarged by 20% for each scrolling.

In a case where the enlarged region 605 is desired to be changed, for example, the examiner moves the mouse cursor 608 to a position at which the image is desired to be enlarged, and rotates the mouse wheel. In this case, the processor 20 changes the center position of the enlarged region in association with the movement of the mouse cursor 608. In addition, the processor 20 may change the enlarged region in a case where a drag operation is performed in a state where the mouse cursor 608 overlaps the image. In addition, the processor 20 may set the enlarged region centering on the position at which clicking is performed on the image. Meanwhile, an example in which a mouse is used as an instruction reception unit is described, but other user interfaces such as a touch panel and a keyboard may be used.

Figure 19:
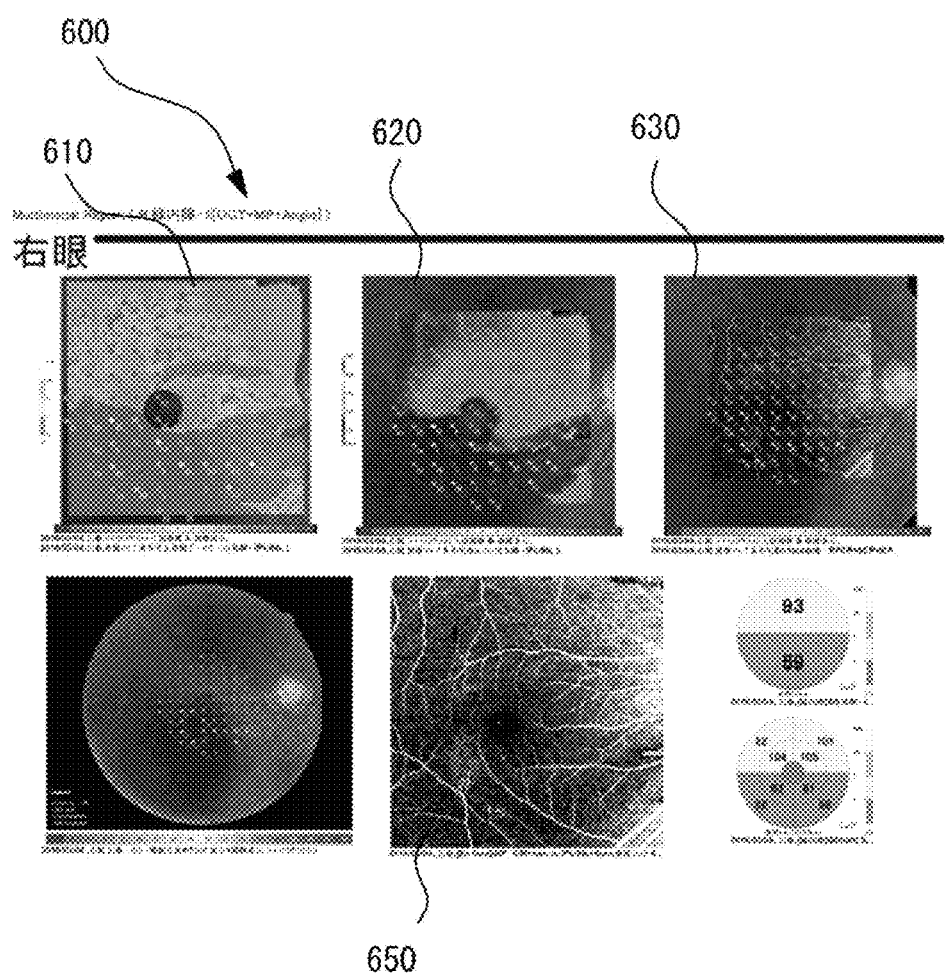
FIG. 19 illustrates an example of a report output screen.

FIG. 19 illustrates an example of the report 600 when a portion of image data is enlarged as described above. In the report 600 of FIG. 19, three pieces of image data disposed on the upper side, among the six pieces of image data, are partially enlarged.

An examiner may change an enlargement rate and an enlarged region 605 of one piece of image data of the report 600, or may change enlargement rates and enlarged regions 605 of the other pieces of image data in accordance with the one piece of image data. For example, in a case where a plurality of pieces of image data of the report 600 are selected, the enlargement rate and the movement of the enlarged region 605 may be synchronized with each other. For example, in a case where three of a registration image 610, a registration image 620, and a registration image 630 are selected, the processor 20 may enlarge the registration image 620 and the registration image 630 at the same enlargement rate and with respect to the same enlarged region in accordance with the enlargement of the registration image 610.

In addition, the processor 20 may change enlargement rates and enlarged regions 605 of the other pieces of image data in accordance with the magnification of specific image data on the report 600. For example, in a case where a motion contrast image 650 of FIG. 18 is image data acquired in a range of 9 mm×9 mm on a fundus centering on a macula, the display of the image 610 may be changed so that the range of 9 mm×9 mm on the fundus is displayed centering on the macula seen in the registration image 610 based on a fundus camera image. Thereby, the examiner can observe the registration image 610 at the same enlargement rate as that of the motion contrast image 650, and easily confirms a relationship between the motion contrast image 650 and the registration image 610 based on the fundus camera image.

As described above, a portion of image data on the report 600 can be enlarged, and thus a space for displaying the other images is not reduced as compared to a case where the entire image is enlarged. Accordingly, it is possible to increase the visibility of the image data without damaging information of the report 600. In addition, a registration image is displayed in an enlarged manner, and thus the examiner can confirm a superimposed portion of the registration image in more detail.

Meanwhile, the processor 20 may be capable of changing the size of a display frame of an image. For example, in a case where the edge of the image is dragged, the processor 20 may change the size of the display frame. In this case, the processor 20 may enlarge or reduce the entire image in accordance with the change in the size of the display frame.

Meanwhile, in a case where the superimposed portion of the registration image is clicked in the report output screen, the processor 20 may enlarge the image to such a size that the superimposed portion is fit tightly into the display frame of the image.

Incidentally, the present disclosure discloses the following aspects:

(1) An ophthalmic image processing apparatus that processes pieces of image data of a subject eye which are acquired by a plurality of ophthalmic examination apparatuses including a first ophthalmic examination apparatus obtaining first image data of the subject eye and a second ophthalmic examination apparatus obtaining second image data of the subject eye, the ophthalmic image processing apparatus comprising:
  setting means for setting image types in the first image data and the second image data that form a registration image; and image processing means for generating the registration image in which the first image data and the second image data which correspond to the image types set by the setting means are superimposed on each other, and outputs the generated registration image.

(2) The ophthalmic image processing apparatus according to (1), wherein
  the setting means changes setting of an order in which the first image data and the second image data are superimposed on each other in the generation of the registration image, and
  the image processing means generates the registration image based on the order of which the setting is changed.

(3) The ophthalmic image processing apparatus according to (1) or (2), wherein
  the setting means changes setting of a transmittance of at least one of the first image data and the second image data in the generation of the registration image, and
  the image processing means generates the registration image based on the transmittance of which the setting is changed.

(4) The ophthalmic image processing apparatus according to any one of (1) to (3), wherein
  the setting means is further capable of changing setting of at least one of a brightness and a contrast with respect to at least one of the first image data and the second image data in the generation of the registration image, and
  the image processing means generates the registration image based on at least one of the brightness and the contrast of which the setting is changed.

(5) The ophthalmic image processing apparatus according to any one of (1) to (4), wherein
  the setting means sets a superimposition region in which the first image data and the second image data are superimposed on each other, in the generation of the registration image, and
  the image processing means generates the registration image based on the set superimposition region.

(6) The ophthalmic image processing apparatus according to any one of (1) to (5), wherein the image processing means generates a report including the registration image and another image different from the registration image.

(7) The ophthalmic image processing apparatus according to (6),
  wherein the setting means is further capable of setting a type of another image.

(8) The ophthalmic image processing apparatus according to any one of (1) to (7),
  wherein the image processing means
  acquires, from a storage unit, as the first image data, first map image data which is a map image of the subject eye acquired by the first ophthalmic examination apparatus and first front image data which is associated with the first map image data, the first front image being a front image of the subject eye acquired by the first ophthalmic examination apparatus,
  acquires, from the storage unit, second map image data which is a map image of the subject eye acquired by the second ophthalmic examination apparatus and second front image data which is a front image of the subject eye acquired by the second ophthalmic examination apparatus, as the second image data, and
  generates and outputs a registration image in which the first map image data, the first front image data, the second map image data, and the second front image data are superimposed on each other.

(9) The ophthalmic image processing apparatus according to (8), wherein the setting means is capable of changing setting of an image type in at least one of the first map image data and the second map image data.

(10) The ophthalmic image processing apparatus according to any one of (1) to (9), wherein the first ophthalmic examination apparatus is an ophthalmic OCT device, and the second ophthalmic examination apparatus is a visual field examination apparatus.

(11) The ophthalmic image processing apparatus according to (10), wherein the image processing means generates and outputs a registration image in which first image data which is an OCT two-dimensional image of the subject eye acquired by the ophthalmic OCT device and second image data which is a map image of the subject eye acquired by the visual field examination apparatus are superimposed on each other.

(12) The ophthalmic image processing apparatus according to (11), wherein the OCT two-dimensional image is map image data of an OCT.

(13) The ophthalmic image processing apparatus according to (11), wherein the OCT two-dimensional image is OCT En face image data.

(14) The ophthalmic image processing apparatus according to (13), wherein the En face image data is En face image data related to a specific layer.

(15) The ophthalmic image processing apparatus according to (13), wherein the En face image data is OCT motion contrast En face image data.

(16) The ophthalmic image processing apparatus according to (8),
  wherein the image processing means performs alignment between the first front image data and the second front image data to thereby perform alignment between the first map image data and the second map image data.

(17) The ophthalmic image processing apparatus according to any one of (1) to (16), wherein
  the image processing means is an image processing means that generates a registration image in which third image data which is image data of the subject eye acquired by a third ophthalmic examination apparatus, different from the first ophthalmic examination apparatus and the second ophthalmic examination apparatus, and the first image data which is image data of the subject eye acquired by the first ophthalmic examination apparatus are superimposed on each other, and
the setting means is capable of changing an image type of an image superimposed on the first image data between the second image data and the third image data.
(18) The ophthalmic image processing apparatus according to any one of (1) to (17), wherein the first ophthalmic examination apparatus is an ophthalmic OCT device, the second ophthalmic examination apparatus is a visual field examination apparatus, and the third ophthalmic examination apparatus is a fundus imaging apparatus for capturing a fundus front image.
(19) The ophthalmic image processing apparatus according to (18),
wherein the third ophthalmic examination apparatus is any one of a fundus camera and an SLO.
(20) The ophthalmic image processing apparatus according to any one of (1) to (19),
wherein the setting means receives an instruction from an examiner for changing setting of the registration image in a state where the registration image is displayed on a display unit, and changes the setting of the registration image, and
wherein the image processing means generates the registration image based on the change of the setting.
(21) The ophthalmic image processing apparatus according to (20),
wherein the setting means receives an instruction from the examiner for selecting image data constituting the registration image, and
wherein the image processing means generates the registration image based on the selection which is set by the setting means.
(22) The ophthalmic image processing apparatus according to any one of (1) to (21), wherein the setting means includes instruction reception means that receives an instruction from an examiner, and performs a setting process based on an instruction signal received from the instruction reception means.
(23) The ophthalmic image processing apparatus according to any one of (1) to (22), wherein the image processing means generates a difference image based on a difference between the first image data and the second image data in a state where the first image data and the second image data are superimposed on each other, and outputs the difference image.
(24) The ophthalmic image processing apparatus according to (1), wherein
the image processing means processes image data of the subject eye acquired by the ophthalmic examination apparatus to thereby generate a report including the image data,
the setting means sets an examination date of the image data which is output as the report, and
the image processing means acquires image data on the examination date set by the setting means or within a predetermined period of time based on the examination date from the storage unit, and generates and outputs a report based on the acquired image data.
(25) The ophthalmic image processing apparatus according to (1), wherein image processing means processes image data of the subject eye acquired by the ophthalmic examination apparatus to thereby generate a report including the image data, enlarges a portion of the image data, and displays the enlarged portion on the report.

(26) An ophthalmic image processing apparatus that processes image data of a subject eye which is acquired by an ophthalmic examination apparatus, the ophthalmic image processing apparatus comprising:
image processing means for processing the image data of the subject eye which is acquired by the ophthalmic examination apparatus to thereby generate a report including the image data; and
setting means for setting an examination date of the image data which is output as the report,
wherein the image processing means acquires image data on the examination date set by the setting means or within a predetermined period of time based on the examination date from the storage unit, and generates and outputs a report based on the acquired image data.
(27) The ophthalmic image processing apparatus according to (26), wherein
the setting means is capable of changing an examination date of image data to be output as the report, and
the image processing means acquires image data on the examination date changed by the setting means or within a predetermined period of time based on the examination date from the storage unit, and generates and outputs a report based on the acquired image data.
(28) The ophthalmic image processing apparatus according to (26) or (27), wherein the image processing means processes pieces of image data of the subject eye which are acquired by the plurality of ophthalmic examination apparatuses to thereby generate and output a report including the pieces of image data acquired by the plurality of ophthalmic examination apparatuses.
(29) The ophthalmic image processing apparatus according to any one of (26) to (28),
wherein the setting means is capable of manually setting an examination date of image data to be output as the report.
(30) The ophthalmic image processing apparatus according to any one of (26) to (29), wherein the image processing means generates an examination date list capable of being set by the setting means based on examination date data added to the image data of the subject eye which is stored in the storage unit, and selectably displays the generated examination date list on a display unit.
(31) The ophthalmic image processing apparatus according to any one of (26) to (30), wherein
the setting means is further capable of setting an image type of image data to be output as the report, and
the image processing means acquires, from the storage unit, the image data which is image data on the examination date set by the setting means or within a predetermined period of time based on the examination date and which corresponds to the set image type, based on the examination date and the image type which are set by the setting means, and generates and outputs a report based on the acquired image data.
(32) The ophthalmic image processing apparatus according to (26), wherein
the setting means is capable of setting an examination date of image data to be output as the report as a predetermined period of time, and
the image processing means acquires image data within the predetermined period of time set by the setting means from the storage unit, and generates and outputs a report based on the acquired image data.
(33) An ophthalmic image processing apparatus that processes pieces of image data of a subject eye which are acquired by a plurality of ophthalmic examination apparatuses, the ophthalmic image processing apparatus comprising:
 image processing means for generating a registration image in which first image data which is OCT En face image data of the subject eye acquired by an ophthalmic OCT device and second image data which is a map image of the subject eye acquired by a visual field examination apparatus are superimposed on each other.

(34) The ophthalmic image processing apparatus according to (33), wherein the En face image data is En face image data related to a specific layer.

(35) The ophthalmic image processing apparatus according to (1), wherein the En face image data is OCT motion contrast En face image data.

(36) An ophthalmic image processing apparatus that processes pieces of image data of a subject eye which are acquired by a plurality of ophthalmic examination apparatuses, the ophthalmic image processing apparatus comprising:
 image processing means for generating a registration image in which first image data which is an OCT two-dimensional image of the subject eye acquired by an ophthalmic OCT device and second image data which is a blood flow map image of the subject eye acquired by an ophthalmic blood flow measurement apparatus are superimposed on each other.

(37) An ophthalmic image processing apparatus that processes pieces of image data of a subject eye which are acquired by a plurality of ophthalmic examination apparatuses, the ophthalmic image processing apparatus comprising:
 image processing means for generating a registration image in which first image data which is a map image of the subject eye acquired by a visual field examination apparatus and second image data which is a blood flow map image of the subject eye acquired by an ophthalmic blood flow measurement apparatus are superimposed on each other.

(38) An ophthalmic image processing apparatus that processes image data of a subject eye which is acquired by an ophthalmic examination apparatus, the ophthalmic image processing apparatus comprising:
 image processing means for processing the image data of the subject eye which is acquired by the ophthalmic examination apparatus to thereby generate a report including the image data,
 wherein the image processing means enlarges a portion of the image data and displays the enlarged portion on the report.

(39) The ophthalmic image processing apparatus according to (38), further comprising:
 instruction reception means for receiving an instruction signal which is output from operation means in accordance with an examiner's operation,
 wherein the image processing means enlarges a portion of the image data and displays the enlarged portion on the report based on an instruction signal received by the instruction reception means.

(40) The ophthalmic image processing apparatus according to (38) or (39),
 wherein the image processing means is capable of changing a magnification of the image data displayed on the report.

(41) The ophthalmic image processing apparatus according to any one of (38) to (40), wherein the image processing means is capable of changing an enlarged region of the image data displayed on the report.

(42) The ophthalmic image processing apparatus according to any one of (38) to (41), wherein the image processing means is individually changing magnifications and/or enlarged regions of a plurality of pieces of image data on the report.

(43) The ophthalmic image processing apparatus according to any one of (38) to (42),
 wherein the image processing means synchronizes magnifications and/or enlarged regions of at least two pieces of image data with each other.

(44) The ophthalmic image processing apparatus according to any one of (38) to (43), wherein the image processing means performs conformation to the magnification and/or the enlarged region of image data having a narrow imaging range among the at least two pieces of image data.

(45) The ophthalmic image processing apparatus according to any one of (39) to (44),
 wherein the image processing means selects at least two images of which magnifications and/or enlarged regions are to be synchronized with each other, based on an instruction signal received by the instruction reception means.

(46) The ophthalmic image processing apparatus according to any one of (39) to (45), wherein
 the instruction reception means receives an instruction signal for selecting an image type of the image data to be output as the report, and
 the image processing means displays the image data of the selected image type on the report, based on the instruction signal received by the instruction reception means.

What is claimed is:

1. An ophthalmic image processing apparatus that processes pieces of image data of a subject eye which are acquired by a plurality of ophthalmic examination apparatuses including a first ophthalmic examination apparatus obtaining first image data of the subject eye and a second ophthalmic examination apparatus obtaining second image data of the subject eye, the ophthalmic image processing apparatus comprising:
 a processor; and
 memory storing computer readable instructions, when executed by the processor, causing the ophthalmic image processing apparatus to execute:
 setting process of setting image types for the first image data and the second image data that form a registration image;
 acquiring, from a storage unit, as the first image data, first map image data of the subject eye acquired by the first ophthalmic examination apparatus and first fundus front image data that is associated with the first map image data, the first fundus front image data being a first fundus front image of the subject eye acquired by the first ophthalmic examination apparatus;
 acquiring, from the storage unit, as the second image data, second map image data that is a map image of the subject eye acquired by the second ophthalmic examination apparatus and second fundus front image data which is a second fundus front image of the subject eye acquired by the second ophthalmic examination apparatus;
 adjusting a magnification between the first fundus front image and the second fundus front image to correct a deviation in a magnification between a first map image associated with the first map image data and a second map image associated with the second map image data;

and;
  image processing process of generating the registration image in which the first image data and the second image data which correspond to the image types set in the setting process are superimposed on each other, and outputting the generated registration image;
  wherein the first ophthalmic examination apparatus is an ophthalmic OCT device that generates an OCT image, which is the first map image, and the second ophthalmic examination apparatus is a visual field examination apparatus that generates a visual field analysis map image, which is the second map image, and
  the visual field analysis map image is a visibility map in which measurement values at a plurality of visual field measurement points are displayed, a two-dimensionally displayed color map that is color coded in accordance with visibility measurement values at a plurality of visual field measurement points, or a map corresponding to a fixation view test.

2. The ophthalmic image processing apparatus according to claim 1, wherein
  the setting process changes setting of an order in which the first image data and the second image data are superimposed on each other in the generation of the registration image, and
  the image processing process generates the registration image based on the order of which the setting is changed.

3. The ophthalmic image processing apparatus according to claim 1, wherein
  the setting process changes setting of a transmittance of at least one of the first image data and the second image data in the generation of the registration image, and
  the image processing process generates the registration image based on the transmittance of which the setting is changed.

4. The ophthalmic image processing apparatus according to claim 1, wherein
  the setting process changes setting of at least one of a brightness and a contrast with respect to at least one of the first image data and the second image data in the generation of the registration image, and
  the image processing process generates the registration image based on at least one of the brightness and the contrast of which the setting is changed.

5. The ophthalmic image processing apparatus according to claim 1, wherein
  the setting process sets a superimposition region in which the first image data and the second image data are superimposed on each other, in the generation of the registration image, and
  the image processing process generates the registration image based on the set superimposition region.

6. The ophthalmic image processing apparatus according to claim 1, wherein the image processing process generates a report including the registration image and another image different from the registration image.

7. The ophthalmic image processing apparatus according to claim 1, wherein the image processing process:
  generates and outputs the registration image in which the first map image data, the first front image data, the second map image data, and the second front image data are superimposed on each other.

8. The ophthalmic image processing apparatus according to claim 7, wherein the setting process changes setting of an image type in at least one of the first map image data and the second map image data.

9. The ophthalmic image processing apparatus according to claim 1, wherein the first image data is an OCT two-dimensional image of the subject eye acquired by the ophthalmic OCT device and wherein the OCT two-dimensional image is OCT map image data.

10. The ophthalmic image processing apparatus according to claim 1, wherein the first image data is an OCT two-dimensional image of the subject eye acquired by the ophthalmic OCT device and wherein the OCT two-dimensional image is OCT En face image data.

11. The ophthalmic image processing apparatus according to claim 10, wherein the En face image data is En face image data related to a specific layer.

12. The ophthalmic image processing apparatus according to claim 10, wherein the En face image data is OCT motion contrast En face image data.

13. The ophthalmic image processing apparatus according to claim 1, wherein the image processing process generates the registration image in which third image data of the subject eye acquired by a third ophthalmic examination apparatus, different from the first ophthalmic examination apparatus and the second ophthalmic examination apparatus, and the first image data are superimposed on each other, and
  wherein the setting process changes an image type of an image superimposed on the first image data between the second image data and the third image data.

14. The ophthalmic image processing apparatus according to claim 13, wherein the first ophthalmic examination apparatus is an ophthalmic OCT device, the second ophthalmic examination apparatus is a visual field examination apparatus, and the third ophthalmic examination apparatus is a fundus imaging apparatus for capturing a fundus front image.

15. The ophthalmic image processing apparatus according to claim 1, wherein the setting process receives an instruction from an examiner, and performs a setting based on the received instruction.

16. The ophthalmic image processing apparatus according to claim 1, wherein the image processing process generates a difference image based on a difference between the first image data and the second image data in a state where the first image data and the second image data are superimposed on each other, and outputs the difference image.

17. The ophthalmic image processing apparatus according to claim 1, wherein image processing process processes image data of the subject eye acquired by the ophthalmic examination apparatus to generate a report including the image data, enlarges a portion of the image data, and displays the enlarged portion on the report.

18. The ophthalmic image processing apparatus according to claim 1, wherein the OCT image superimposed with the visual field analysis map image is switchable between an analysis image and an OCT En face image.

19. The ophthalmic image processing apparatus according to claim 1, wherein the processor selectively displays a plurality of image types related to the visual field analysis map image.

* * * * *